US009676829B2

(12) United States Patent
Weel-Sneve et al.

(10) Patent No.: US 9,676,829 B2
(45) Date of Patent: Jun. 13, 2017

(54) ANTIBACTERIAL POLYPEPTIDES AND USE THEREOF

(71) Applicant: Oslo Universitetssykehus HF, Oslo (NO)

(72) Inventors: Ragnhild Weel-Sneve, Oslo (NO); James Alexander Booth, Oslo (NO); Magnar Bjørås, Oslo (NO); Knut Ivan Kristiansen, Oslo (NO)

(73) Assignee: Oslo Universitetssykehus HF, Oslo (NO)

( * ) Notice: Subject to any disclaimer, the term of this patent is extended or adjusted under 35 U.S.C. 154(b) by 34 days.

(21) Appl. No.: 14/496,779

(22) Filed: Sep. 25, 2014

(65) Prior Publication Data

US 2015/0011464 A1 Jan. 8, 2015

Related U.S. Application Data

(62) Division of application No. 13/499,650, filed as application No. PCT/EP2010/064769 on Oct. 4, 2010, now abandoned.

(60) Provisional application No. 61/329,440, filed on Apr. 29, 2010.

(30) Foreign Application Priority Data

Oct. 2, 2009 (EP) ..................................... 09172106

(51) Int. Cl.
   *C07K 14/31* (2006.01)
   *C07K 14/24* (2006.01)
   *C07K 14/245* (2006.01)

(52) U.S. Cl.
   CPC ............ *C07K 14/245* (2013.01); *C07K 14/24* (2013.01)

(58) Field of Classification Search
   CPC ................................ C07K 14/31; C07K 14/24
   See application file for complete search history.

(56) References Cited

U.S. PATENT DOCUMENTS 8,758,764 B2 * 6/2014 Masignani ......... A61K 39/0258
424/185.1
2007/0031874 A1 2/2007 Miller

FOREIGN PATENT DOCUMENTS

WO   WO 00/44906       8/2000
WO   WO 2005/056754 A2 6/2005

OTHER PUBLICATIONS

Bodmann. 2005; Current guidelines for the treatment of severe pneumonia and sepsis. Chemotherapy. 51(5): 227-233.*

Brosius, "Plasmid vectors for the selection of promoters." Gene (Elsevier Science Publishers). 1984. 27(936):151-160.
Brown et al., "Two host-induced *Ralstonia solanacearum* genes, acrA and dinF, encode multidrug efflux pumps and contribute to bacterial wilt virulence." Applied & Environmental Microbiology. 2007. 73(9):2777-2786.
Clark et al., "DNA replication and the division cycle in *Escherichia coli*." Journal of Molecular Biology. 1967. 23:99-112.
Hemm et al., "Small membrane proteins found by comparative genomics and ribosome binding site models." Molecular Biology. 2008. 70(6):1487-1501.
Henestrosa et al., "Identification of additional genes belonging to the LexA regulon in *Escherichia coli*." Molecular Biology. 2000. 35(6):1560-1572.
Rognes, "ParAlign: a parallel sequence alignment algorithm for rapid and sensitive database searches." Nucleic Acids Research. 2001. 29(7):1647-1652.
Saetrom et al., "Predicting non-coding RNA genes in *Escherichia coli* with boosted genetic programming." Nucleic Acids Research. 2005. 33(10):3263-3270.
Seeberg et al., "Excision repair of ultraviolet-irradiated deoxyribonucleic acid in plasmolyzed cells of *Escherichia coli*." Journal of Bacteriology. 1976. 125(3):787-795.
Unoson et al., "A small SOS-induced toxin is targeted against the inner membrane in *Escherichia coli*." Molecular Microbiology. 2008. 70(1):258-270.
Wickens et al., "Flow cytometric investigation of filamentation, membrane patency, and membrane potential in *Escherichia coli* following ciprofloxacin exposure." Antimicrobial Agents and Chemotherapy. 2000. 44(3):682-687.
Wilson et al., "High-frequency generalized transduction by bacteriophage T4." Nature. 1979. 280:80-82.
Database Uniprot: XP-002554069—"The pangenome structure of *Escherichia coli*: comparative genomic analysis of *E. coli* commensal and pathogenic isolates." J. Bacteriol. 190:6881-6893 (2008).
Database Uniprot: XP-002554070—"Identification of genes subject to positive selection in uropathogenic strains of *Escherichia coli*: a comparative genomics approach." Proc. Natl. Acad. Sci. U.S.A. 103:5977-5982(2006).
Database Uniprot: XP-002554071—Submitted (Jun. 2008) to the EMBL/GenBank/DDBJ databses.
Fernandez de Henestrosa et al., Molecular Microbiology, 2000, 35:1560-1572.
Berg et al, Biochemistry Fifth Edition, WH Freeman and Company, New York, pp. 176-177.

(Continued)

*Primary Examiner* — Karen Cochrane Carlson
(74) *Attorney, Agent, or Firm* — Knobbe Martens Olson & Bear LLP

(57) ABSTRACT

The present invention discloses polypeptides with antibacterial properties and use said polypeptides and/or polynucleotides encoding said polypeptides in the preparation of medicament for the treatment of infectious diseases. The inventors also provide vectors encoding and adapted for expression of the polypeptides and polynucleotides of the invention. The vectors may be used in the preparation of a medicament for the treatment of bacterial infections. Further, the vector of the invention may be used to reduce the load of bacteria in food and/or feed.

10 Claims, 23 Drawing Sheets

(56) References Cited

OTHER PUBLICATIONS

Figure 2:
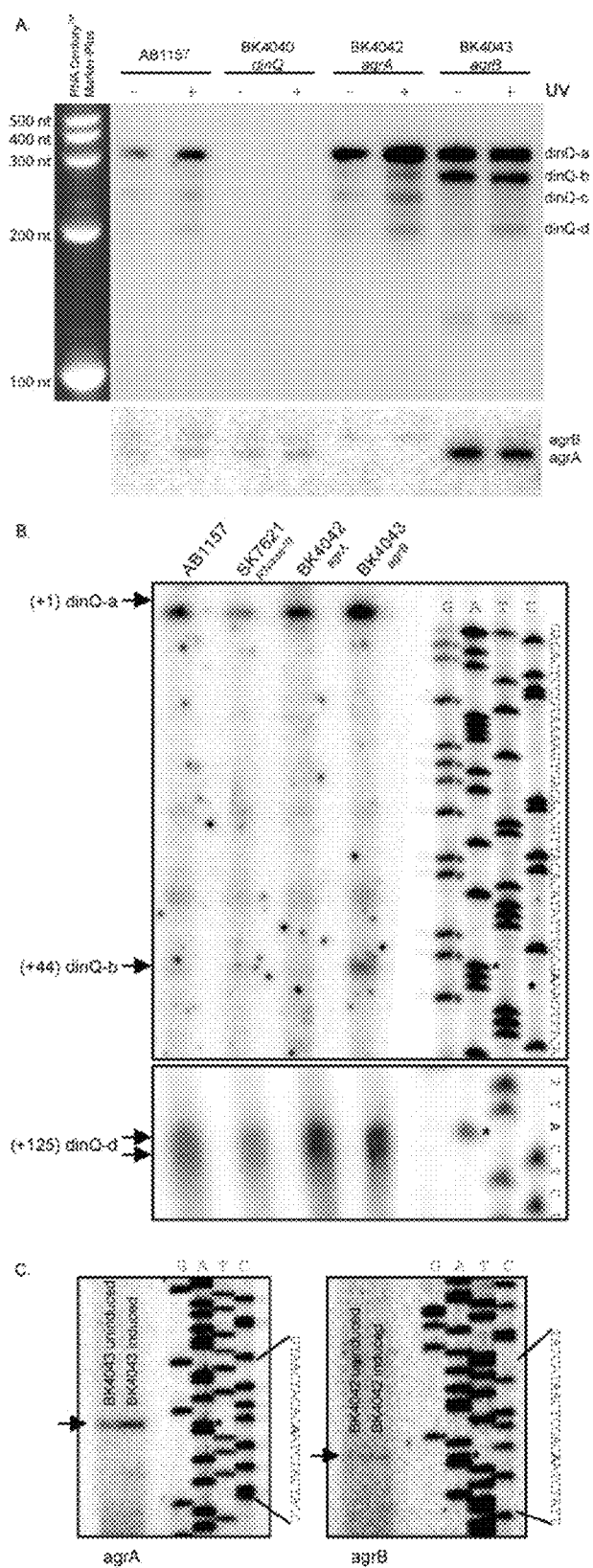

Sleator, Methods in Molecular Biology, 2012, 815:15-24.
Skolnick et al., Trands in Biotech, 2000, 18:34-39.
Weel-Sneve et al., PLoS Genetics, 2013, 9:e1003260.
Elbing et al., Current Protocols in Molecular Biology, 2007, Unit 1.1.1-1.17.8.
Ganoza et al., PNAS, 1985, 82:4587-4591.
Kelly, Molecular Microbiology, 2006, 62:1228-1238.
Wilson et al., Nature, 1979, 280:80-82.

\* cited by examiner

Fig. 1

A

MIDKAIIVLGALIALLELIRFLLQLLN

Hydrophilic (DEKRHQ) in DinQ : 6/27
Hydrophobic (ALIVMF) in DinQ : 20/27
Glycine (G) in DinQ : 1/27

B cisBB  (+1) GUACGCAAUGUGUAAUGCGAGGGCCGCAUCGUUACCCGGCGCACUAAGUCCUGG-CUGAA--ACCGGUGGUGCCGUCAGUGCCU dinQ   (+1) CAGUUAGCUCUGAGGCAUUUUCACUCUGGGCAAUGCGCAUAAACGCUGUCAAGUCCUGGUCAGAAGUACGGUGGUGCCGUUAACUGAU

Fig. 8

A. MIDKAIIVKGALIALLELIRFLLQLLN
---HHHHHHHHHHHHHHHHHHHHHHH--
997689999999999999999998508

ANTIBACTERIAL POLYPEPTIDES AND USE THEREOF

CROSS-REFERENCE TO RELATED APPLICATIONS

This application is a divisional of and claims the benefit and priority to U.S. patent application Ser. No. 13/499,650, filed on May 11, 2012, which is a U.S. National Phase application of PCT International Application Number PCT/EP2010/064769, filed on Oct. 4, 2010, designating the United States of America and published in the English language, which is an International Application of and claims the benefit of priority to European Patent Application No. 09172106.8, filed on Oct. 2, 2009, and U.S. Provisional Application No. 61/329,440, filed on Apr. 29, 2010. The disclosures of the above-referenced applications are hereby expressly incorporated by reference in their entireties.

REFERENCE TO SEQUENCE LISTING

The present application is being filed along with a sequence listing in electronic format. The sequence listing is provided as a file entitled SeqList_PLOUG83_007D1SUB.txt, created Mar. 9, 2017 which is 18 KB in size. The information in the electronic format of the sequence listing is incorporated herein by reference in its entirety.

FIELD OF THE INVENTION

The present invention discloses polypeptides with antibacterial properties and use of said polypeptides and/or polynucleotides encoding said polypeptides in the preparation of medicament for the treatment of infectious diseases. The inventors also provide vectors encoding and adapted for expression of the polypeptides and polynucleotides of the invention. The vectors may be used in the preparation of a medicament for the treatment of bacterial infections. Further, the vector of the invention may be used to reduce the load of bacteria in food and/or feed.

BACKGROUND

The discovery of antibiotics in the mid 1950s represented a major advance in human health. Contrasting the benefits, however, antibiotic-resistant bacteria challenge the use of drugs by undermining the effectiveness of current treatment options. Strains resistant to all commonly used antibiotics have been identified in every significant disease caused by bacteria. This is underscoring the importance of developing new strategies to treat disease with an underlying bacterial infection, including strategies to combat the emerging treat of antibiotic-resistant bacteria. Accordingly, therapeutic strategies to kill antibiotic-resistant bacteria and combating the evolution of antibiotic resistance have a vast commercial potential.

Exposure of *Escherichia coli* to agents that damage DNA or interfere with DNA replication induces the expression of a set of genes called the SOS response. Many of the genes induced as part of the SOS response codes for proteins involved in DNA repair, recombination, DNA replication and cell division. The key regulators of SOS induction are the RecA protein and the LexA repressor. Although the expression of the LexA-regulated genes in *E. coli* has been extensively studied, the roles of several SOS genes are still unknown.

RecA protein and the LexA repressor are known regulators of SOS induction. Following DNA damage RecA and single-stranded DNA forms a nucleoprotein filament which catalyzes autocleavage of LexA repressor, leading to induction of more than 30 genes including recA and lexA. The kinetics of SOS induction in *E. coli*, measured by monitoring LexA cleavage after UV irradiation is understood in detail.

In addition to the more than 30 genes under direct control of LexA repressor, the transcriptional level of more than 1000 genes in *E. coli* are affected by treatment of DNA damaging agents. The translational levels of several proteins are also known to be upregulated by DNA damage in a LexA independent, but RecA dependent manner. One such example is the Eda protein, the last enzyme in the Entner-Doudoroff pathway, whose function is necessary for the recovery of respiration following the SOS response.

The SOS inducible dinQ gene in *E. coli* was identified in a search for new lexA regulated genes (Fernandez de Henestrosa et al., Mol Microbiol 2000). The dinQ gene was found in the 823 bp arsR-gor intergenic region encoding a ~330 nt transcript with a HI=4.83. No biological function, phenotype or significant homologies to proteins with known function were associated with the dinQ sequence (Fernandez de Henestrosa et al., Mol Microbiol 2000). Except for the dinQ gene, no other genes have been reported in the arsR-gor intergenic region.

Hemm et al (2008) addressed the expression of a panel of short ORFs in *E. coli* including the dinQ gene but the study failed to detect products of DinQ.

The emergence of antibiotic resistant bacteria poses a serious threat to human health, and there is a remaining need for the provision of new antibiotics, novel therapeutic strategies and approaches to combat the emerging antibiotic resistant bacteria that poses a serious threat to human health.

SUMMARY OF THE INVENTION

The object of the present invention is to provide new antibiotics, novel therapeutic strategies and approaches to combat the bacteria, in particular pathogenic bacteria that pose a serious threat to human health, such as antibiotic resistant bacteria.

The present inventors disclose polypeptides with antibacterial properties and use said polypeptides and/or polynucleotides encoding said polypeptides in the preparation of medicament for the treatment of infectious diseases. Further, the inventors provide vectors encoding and adapted for expression of the polypeptides and polynucleotides of the invention. The vectors may be used in the preparation of a medicament for the treatment of bacterial infections. Further, the vector of the invention may be used to reduce the load of bacteria in food and/or feed.

A first aspect of the present invention relates to an isolated antibacterial polypeptide selected from the group consisting of (a) a polypeptide encoded by SEQ ID NO: 1 (dinQ gene sequence), (b) a functionally equivalent subsequence of (a) of at least 15 amino acids (c) a functionally equivalent polypeptide with a sequence identity of at least 85% to (a) or (b).

In one embodiment of the invention the isolated antibacterial polypeptide is selected from the group consisting of SEQ ID NO:3 (DinQ ORF-I peptide), SEQ ID NO:5 (DinQ ORF-II peptide), SEQ ID NO:7 (DinQ ORF-III peptide), SEQ ID NO:9 (DinQ ORF-IV peptide), SEQ ID NO:11

(DinQ ORF-V peptide) and SEQ ID NO:17 (DinQ ORF-V peptide with N-terminal Met).

A second aspect of the present invention relates to a synthetic antibacterial polypeptide with an amino acid sequence set forth by any of the polypeptides described above.

In one embodiment of the present invention the polypeptide is at least bacteriostatic and/or bactericidal.

A third aspect of the present invention relates to an isolated polynucleotide sequence comprising a nucleic acid sequence encoding an antibacterial polypeptide of the invention.

A fourth aspect of the present invention relates to a vector comprising a nucleic acid sequence encoding an antibacterial polypeptide of the present invention.

In a preferred embodiment, the vector is adapted for expression of said polypeptide. In another embodiment, the vector is a phage.

In a fifth aspect of the present invention, a vector is for use as a medicament for the treatment of a bacterial infection.

In a preferred embodiment the vector is for use as a medicament for the treatment of bacterial infection. In another embodiment, the vector is for reducing the load of contaminating bacteria in food products or feed products.

In yet another aspect of the present invention relates to an antibacterial polypeptide of the invention for use as a medicament.

A preferred embodiment provides the antibacterial polypeptide of the invention for use as a medicament in for treatment of a bacterial infection.

A further aspect concerns, the use of the antibacterial polypeptide of the invention for the preparation of a medicament for the treatment of a bacterial infection.

One aspect of the invention concerns the antibacterial polypeptide of the invention for use in the treatment of sepsis.

A further aspect of the present invention relates to a method for reducing the load of or inhibition of propagation of a bacterium by increasing the activity of an antibacterial peptide encoded by SEQ ID NO:1 (dinQ gene sequence) in said bacterium.

In one embodiment the method comprises introducing a polypeptide in said bacterium, wherein said polypeptide is selected from the group consisting of (a) a polypeptide encoded by SEQ ID NO:1 (dinQ gene sequence), (b) a functionally equivalent subsequence of (a) of at least 15 amino acids (c) a functionally equivalent polypeptide with a sequence identity of at least 85% to (a) or (b).

In a particular embodiment the polypeptide is introduced into the said bacterium using a vector adapted for expression of said polypeptide.

A final aspect of the present invention relates to the use of the antibacterial polypeptide or polynucleotide encoding said polypeptide for reducing the load of or inhibiting the propagation of a bacterium.

DETAILED DESCRIPTION OF THE INVENTION

Sequences

SEQ ID NO: 1
SEQ ID NO: 1 corresponds to the dinQ gene sequence.
SEQ ID NO: 2
SEQ ID NO: 2 corresponds to the nucleic acid sequence encoding the dinQ I polypeptide (ORF-I)
SEQ ID NO: 3
SEQ ID NO: 3 corresponds to the amino acid sequence of the dinQ I polypeptide (ORF-I).
SEQ ID NO: 4
SEQ ID NO: 4 corresponds to the nucleic acid sequence encoding the dinQ II polypeptide (ORF-II)
SEQ ID NO: 5
SEQ ID NO: 5 corresponds to the amino acid sequence of the dinQ II polypeptide (ORF-II).
SEQ ID NO: 6
SEQ ID NO: 6 corresponds to the nucleic acid sequence encoding the dinQ III polypeptide (ORF-III).
SEQ ID NO: 7
SEQ ID NO: 7 corresponds to the amino acid sequence of the dinQ III polypeptide (ORF-III).
SEQ ID NO: 8
SEQ ID NO: 8 corresponds to the nucleic acid sequence encoding the dinQ IV polypeptide (ORF-IV).
SEQ ID NO: 9
SEQ ID NO: 9 corresponds to the amino acid sequence of the dinQ IV polypeptide (ORF-IV).
SEQ ID NO: 10
SEQ ID NO: 10 corresponds to the nucleic acid sequence encoding the dinQ V polypeptide (ORF-V).
SEQ ID NO: 11
SEQ ID NO: 11 corresponds to the amino acid sequence of the dinQ V polypeptide (ORF-V).
SEQ ID NO: 12
SEQ ID NO: 12 corresponds to the nucleic acid sequence encoding the argA transcript.
SEQ ID NO: 13
SEQ ID NO: 13 corresponds to the nucleic acid sequence encoding the argB transcript.
SEQ ID NO: 14
SEQ ID NO: 14 corresponds to the nucleic acid sequence encoding the dinQ-a transcript.
SEQ ID NO: 15
SEQ ID NO: 15 corresponds to the nucleic acid sequence encoding the dinQ-b transcript. The dinQ-b transcript is also referred to as the +44 dinQ transcripts.
SEQ ID NO: 16
SEQ ID NO: 16 corresponds to the nucleic acid sequence encoding the dinQ-d transcript.
SEQ ID NO: 17
SEQ ID NO: 17 corresponds to the amino acid sequence encoding the dinQ V polypeptide (ORF-V) in which the N-terminal Val-residue has been substituted with a Met-residue.
SEQ ID NO: 18
The plasmid pORF5 which is packed into the phagmid particles and ultimately is responsible for the expression of ORF-V inside of E. coli.
SEQ ID NO: 19
Variant of the amino acid sequence of the dinQ V polypeptide (ORF-V), where the Gly in position 10 of the peptide have been substituted with a Lys.
SEQ ID NO: 20
Variant of the amino acid sequence of the dinQ V polypeptide (ORF-V), where the Leu in position 23 of the peptide have been substituted with an Ile.
SEQ ID NO: 21
Variant of the amino acid sequence of the dinQ V polypeptide (ORF-V), where the Ile in position 7 of the peptide have been substituted with a Val.

SEQ ID NO: 22

Variant (double mutant) of the amino acid sequence of the dinQ V polypeptide (ORF-V), where the Leu in position 12 of the peptide have been substituted with an Be, and the Ile in position 13 of the peptide have been substituted with a Val.

DEFINITIONS

Prior to discussing the present invention in further details, the following terms and conventions will first be defined:

Sequence Identity

The term "sequence identity" indicates a quantitative measure of the degree of homology between two amino acid sequences or between two nucleic acid sequences of equal length. If the two sequences to be compared are not of equal length, they must be aligned to give the best possible fit, allowing the insertion of gaps or, alternatively, truncation at the ends of the polypeptide sequences or nucleotide sequences. The sequence identity can be calculated as $$\frac{(N_{ref} - N_{dif})100}{N_{ref}},$$

wherein Ndif is the total number of non-identical residues in the two sequences when aligned and wherein Nref is the number of residues in one of the sequences. Hence, the DNA sequence AGTCAGTC will have a sequence identity of 75% with the sequence AATCAATC (Ndif=2 and Nref=8). A gap is counted as non-identity of the specific residue(s), i.e. the DNA sequence AGTGTC will have a sequence identity of 75% with the DNA sequence AGTCAGTC (Ndif=2 and Nref=8).

With respect all embodiments of the invention relating to nucleotide sequences, the percentage of sequence identity between one or more sequences may also be based on alignments using any suitable software such as the clustalW software with default settings. For nucleotide sequence alignments these settings are: Alignment=3Dfull, Gap Open 10.00, Gap Ext. 0.20, Gap separation Dist. 4, DNA weight matrix: identity (IUB).

Alternatively, and as illustrated in the examples, nucleotide sequences may be analysed using any suitable software such as DNASIS Max. This service is based on the two comparison algorithms called Smith-Waterman (SW) and ParAlign. The first algorithm was published by Smith and Waterman (1981) and is a well established method that finds the optimal local alignment of two sequences. The other algorithm, ParAlign, is a heuristic method for sequence alignment; details on the method is published in Rognes (2001). Default settings for score matrix and Gap penalties as well as E-values were used.

When referring to complementary sequences, the following base pairing rules can be applied, G pairs to C and U, A pairs to T and U. "Nucleic acids sequence" and "polynucleotide sequence" are interchangeable terms in the context of the present invention.

Non-Coding RNA

The term "non-coding RNA" (ncRNA) is a functional RNA molecule that is not translated into a protein. The term small RNA (sRNA) is often used for bacteria. The DNA sequence from which a non-coding RNA is transcribed as the end product is often called an RNA gene or non-coding RNA gene.

In one embodiment of the present invention "non-coding RNA" refers to a transcript selected from the group consisting of transcripts of agrA and agrB and variants thereof Oligonucleotides The oligonucleotides of the invention may comprise RNA monomers, DNA monomers, LNA monomers, PNA monomers etc. In a preferred embodiment, the oligonucleotide is built from RNA monomers. In another preferred embodiment, the oligonucleotide is built from DNA monomers.

The oligonucleotide may comprise non-natural nucleotides for better hybridisation or increased biostability. Preferred non-natural nucleotides are LNA, INA, FANA, ENA, PNA and morpholino nucleotides. Also 2-O substituted nucleotides may be used, e.g. 2-O-methyl or 2-O-methoxyethyl. Preferably, the exogenously synthesized oligonucleotide is minimized in size for better delivery.

Control of Bacterial Growth

The term "control of bacterial growth", as used here, means to inhibit or prevent growth of bacteria. This control is affected in two basic ways: (1) by killing the bacteria or (2) by inhibiting the growth of the bacteria.

Bacteria

The term "target pathogen" or "target bacteria" or "bacteria" refers bacteria that may cause illness in a subject. In one preferred embodiment of the present invention the bacterium is a gram negative, even more preferably the bacterium is selected from the group of pathogenic *E. coli, Salmonella, Campylobacter, Shigella, Klebsiella, Pseudomonas*, and *Streptococcus*.

Antibiotic Resistance

In the sense of the present invention antibiotic resistance refers to the ability of a bacteria to withstand the effects of an antibiotic. It is a specific type of drug resistance. Antibiotic resistance evolves naturally via natural selection acting upon random mutation, but it could also be engineered by applying an evolutionary stress on a population. Once such a gene is generated, bacteria can then transfer the genetic information in a horizontal fashion (between individuals) for example by plasmid exchange. Antibiotic resistance can also be introduced artificially into a bacteria through transformation protocols.

Bactericidal

The term "bactericidal" is to be understood as capable of killing bacterial cells. Thus, a bactericide or bacteriocide is a substance or composition that kills bacteria.

Bacteriostatic

The term "bacteriostatic" refers to the property of an agent or composition to inhibit the growth or multiplication of bacteria. A bacteriostatic antibiotic typically limits the growth of bacteria by interfering with bacterial protein production, DNA replication, or other aspects of bacterial cellular metabolism. Thereby bacteriostatic antibiotics inhibit growth and reproduction of bacteria without killing them; killing is done by bactericidal agents. However, there is not always a precise distinction between them and bactericides; high concentrations of most bacteriostatic agents are also bactericidal, whereas low concentrations of bacteriocidal agents are only bacteriostatic.

Toxicity

Toxicity is here defined as the inhibition of or inability of a bacterium to propagate in the presence of a polypeptide or polynucleotide of the invention, for example on plating on an agar-plate or in an infected wound. It is not necessarily possible to distinguish between bactericidal and bacteriostatic effects of the dinQ polypeptide of the invention.

Infected Subject

Reference to a "subject" includes a human or non-human species including primates, livestock animals e.g. sheep, cows, pigs, horses, donkey, goats, laboratory test animals e.g. mice, rats, rabbits, guinea pigs, hamsters, companion animals e.g. dogs, cats, avian species e.g. poultry birds, aviary birds, reptiles and amphibians. The present invention has applicability in human medicine as well as having livestock and veterinary and wild life applications.

Vector

The term "vector" refers to a DNA molecule used as a vehicle to transfer recombinant genetic material into a host cell. The four major types of vectors are plasmids, bacteriophages and other viruses, cosmids, and artificial chromosomes. The vector itself is generally a DNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell. Vectors called expression vectors (expression constructs) are specifically adapted for the expression of the heterologous sequences in the target cell, and generally have a promoter sequence that drives expression of the heterologous sequences. Simpler vectors called transcription vectors are only capable of being transcribed but not translated: they can be replicated in a target cell but not expressed, unlike expression vectors. Transcription vectors are used to amplify the inserted heterologous sequences. The transcripts may subsequently be isolated and used as templates suitable for in vitro translation systems. The choice of vector employed in embodiments of the present invention depends on the specific application of the vector encoding the polypeptides or polynucleotide of the invention.

Operatively Linked

The term "operatively linked" refers to the connection of elements being a part of a functional unit such as a gene or an open reading frame. Accordingly, by operatively linking a promoter to a nucleic acid sequence encoding a polypeptide the two elements becomes part of the functional unit—a gene. The linking of the expression control sequence (promoter) to the nucleic acid sequence enables the transcription of the nucleic acid sequence directed by the promoter. By operatively linking two heterologous nucleic acid sequences encoding a polypeptide the sequences becomes part of the functional unit—an open reading frame encoding a fusion protein comprising the amino acid sequences encoding by the heterologous nucleic acid sequences. By operatively linking two amino acids sequences, the sequences become part of the same functional unit—a polypeptide. Operatively linking two heterologous amino acid sequences generates a hybrid (fusion) polypeptide.

Phage

A bacteriophage (phage) is any one of a number of viruses that infect bacteria (such as M13). Bacterophages are excellent tools to enter a host cell. The phages functions as a vector for delivery and heterologous expression of the polypeptides of the invention, the polynucleotides of the invention, fragments thereof, or siRNAs. Heterologous expression is from an expression cassette inserted in the genome of the phage. Transcription from the expression cassette may either be constitutive or inducible (such as conditional expression induced by a ligand, for example IPTG).

The invention will hereinafter be described by way of the following non-limiting embodiments.

Exposure of *Escherichia coli* to agents that damage DNA or interfere with DNA replication induces the expression of a set of genes called the SOS response. Many of the genes induced as part of the SOS response code for proteins involved in DNA repair, recombination, DNA replication and cell division. The key regulators of SOS induction are the RecA protein and the LexA repressor.

With the present invention, the inventors disclose functions of one of the LexA-regulated genes in *E. coli*, the dinQ gene (SEQ ID NO:1).

The Polypeptides of the Invention

The main object of the present invention is to provide new antibiotics, novel therapeutic strategies and approaches to combat bacteria, in particular pathogenic bacteria that pose a serious threat human health, such as antibiotic resistant bacteria. In the context of the present invention "polypetides" and "peptides" are interchangeable terms in the context of the present invention.

The inventors discovered that polypeptides encoded by dinQ display antibacterial properties.

The antibacterial dinQ polypeptides are encoded by the dinQ transcripts, which contain two open reading frames (ORFs) encoding peptides of 18 and 49 amino acids (aa), in which the 49 aa ORF contain four potential start codons, ORF-II (or ORF-2) of 49 aa, ORF-III (or ORF-3) of 42 aa, ORF-IV (or ORF-4) of 38 aa and an alternative transcription start codon GTG at ORF-V (or ORF-5) of 27 aa. The inventors have only detected translation of ORF-V in vivo. The structure of the dinQ gene is shown in FIG. 1. None of the dinQ ORFs shows strong homology to any known peptides. Roman numerals and Arabic numerals are used interchangeably to refer to the specific ORFs of dinQ.

The dinQ transcripts encode toxic polypeptides of which one is particularly toxic, the dinQ ORF-V polypeptide (SEQ ID NO:11). Cellular fractionation shows that the DinQ polypeptide peptide localized to the inner membrane (Example 5), over-expression of the polypeptides cause depolarization of the bacterial cell membrane (Example 7) and decreases the cellular ATP concentration (Example 8). Taken together, the data provided by the inventors suggest that the DinQ polypeptides modulate membrane integrity of the bacterium.

Accordingly, one aspect of the present invention relates to an isolated antibacterial polypeptide selected from the group consisting of (a) a polypeptide encoded by SEQ ID NO: 1 (dinQ gene sequence), (b) a functionally equivalent subsequence of (a) of at least 15 amino acids (c) a functionally equivalent polypeptide with a sequence identity of at least 85% to (a) or (b).

In one embodiment, said antibacterial polypeptide is selected from the group consisting of SEQ ID NO:3 (DinQ ORF-I peptide), SEQ ID NO:5 (DinQ ORF-II peptide), SEQ ID NO:7 (DinQ ORF-III peptide), SEQ ID NO:9 (DinQ ORF-IV peptide), SEQ ID NO:11 (DinQ ORF-V peptide) and SEQ ID NO:17 (DinQ ORF-V peptide with N-terminal Met).

In another embodiment, the functionally equivalent polypeptide is selected from the group consisting of SEQ ID NO:19 (G10K variant of DinQ ORF-V peptide), SEQ ID NO:20 (L23I variant of DinQ ORF-V peptide), SEQ ID NO:21 (I7V variant of DinQ ORF-V peptide), and SEQ ID NO:22 (L12I, I13V double mutant variant of DinQ ORF-V peptide). In one embodiment, said antibacterial polypeptide has the amino acid sequence set forth in SEQ ID NO:5 (DinQ ORF-II peptide).

In a preferred embodiment, said antibacterial polypeptide has the amino acid sequence set forth in SEQ ID NO:9 (DinQ ORF-IV peptide).

In another preferred embodiment, said antibacterial polypeptide has the amino acid sequence set forth in SEQ ID NO:11 (DinQ ORF-V peptide).

In a further embodiment, said antibacterial polypeptide has the amino acid sequence set forth in SEQ ID NO:17 (DinQ ORF-V peptide with N-terminal Met). The DinQ peptide set forth in SEQ ID NO: 17 is the form that results from the translation of the DinQ ORF-V using GUG as start codon. When GUG is used as start-codon, it is translated as methionine, although the codon normally encodes a Val. In the prokaryotic translation machinery a distinct tRNA is present that initiates such translation. The DinQ peptide set forth in SEQ ID NO: 17 is also referred to as the wild type DinQ ORF-V peptide herein.

In one embodiment, said antibacterial polypeptide has the amino acid sequence set forth in SEQ ID NO:19 (G10K variant of DinQ ORF-V peptide).

In another embodiment, said antibacterial polypeptide has the amino acid sequence set forth in SEQ ID NO:20 (L23I variant of DinQ ORF-V peptide).

In yet another embodiment, said antibacterial polypeptide has the amino acid sequence set forth in SEQ ID NO:21 (I7V variant of DinQ ORF-V peptide).

In a further embodiment, said antibacterial polypeptide has the amino acid sequence set forth in SEQ ID NO:22 (L12I, I13V double mutant variant of DinQ ORF-V peptide).

The antibacterial polypeptide of the invention may be in the form of isolated polypeptides such as polypeptides isolated from a suitable host adapted for recombinant expression of said polypeptides (biosynthesized). In another embodiment, the antibacterial polypeptides isolated from in vitro translation of polynucleotide encoding said polypeptide. A non-limiting example of in vitro transcription and translation is provided with Example 4.

Another aspect of the present invention concerns a synthetic antibacterial polypeptide with an amino acid sequence set forth in any of the preceding aspect/embodiments. The synthetic peptide may be obtained by standard methods of peptide synthesis known by the skilled person. The polypeptides may comprise natural amino acids and peptidomimetics which may include but not be limited to D-peptides, beta-peptides, peptoids and other suitable peptidomimetics known in the art.

The antibacterial polypeptide of the invention may have bactericidal and/or bacteriostatic properties. Thus, in one embodiment of the present invention, the antibacterial polypeptide of the invention is at least bactericidal or bacteriostatic or poses both properties. In another embodiment, the antibacterial polypeptide of the invention is bactericidal. Thus, in third embodiment, the antibacterial polypeptide of the invention is bacteriostatic.

In one embodiment, the antibacterial polypeptide is bacteriostatic at low concentration levels. In a further embodiment, the antibacterial polypeptide is bacteriocidal at high concentration levels.

The skilled person would know how to use available methodology to assess an expression level that elicits either one of the antibacterial properties, for example by using probes for viability in combination with probes for propagation.

The term "antibacterial polypeptide" refers to any dinQ encoded polypeptide, which can suppress the overall growth a bacterium or composition of bacterial species with at least 1% as compared to a culture grown under similar growth conditions without supplementation of dinQ encoded polypeptides as described herein. Preferred embodiments relates to growth suppression of at least 5%, such 10%, such as 25%, such as 50%, such as 75%, such as 80%, such as 90%, and such as 95%. In a particular preferred embodiment said growth suppression is a total inhibition of growth by 100%. The reduction in the load of the bacteria reflects toxicity of the dinQ polypeptides (bactericidal and/or bacteriostatic properties).

One embodiment of the present invention provide functionally equivalent subsequence of a polypeptide encoded by SEQ ID NO: 1 (dinQ gene sequence), said subsequence having at least the length of 15 amino acids (aa.), such as at least 20 aa., for example at least 25 aa., such as at least 30 aa., for example at least 35 aa., such as at least 40 aa., for example at least 45 amino acids.

In one embodiment, said a polypeptide or functionally equivalent subsequence of (a) is having a sequence identity of at least 85% to (a) or (b), such as at least 90% to (a) or (b), for example at least 95% to (a) or (b), such as at least 97% to (a) or (b), for example at least 98% to (a) or (b), such as at least 99% to (a) or (b).

The subsequence of the polypeptide encoded by SEQ ID NO: 1 has maintained the property of the parent polypeptide in terms of bactericidal and/or bacteriostatic properties (referred to as functionally equivalent). In one embodiment, the bactericidal and/or bacteriostatic activity of the subsequence is increase relative to the parent polypeptide. The bactericidal and/or bacteriostatic may be assessed using method available in the art.

Other dinQ Peptide Variants.

Analysis of the DinQ amino acid sequence using the consensus secondary structure prediction tool Jpred3 reveal that DinQ has high propensity to form a single alpha-helix. All residues except a few on each flanking terminal are predicted with high confidence to belong to the predicted alpha-helix (see FIG. 19, A and Example 17 for further details). The structure may also be predicted using other prediction tools available to the skilled person.

The 3D structure of DinQ provided by the inventors may be used as a pharmacophore to design further antibacterial peptides (DinQ variants) such as a polypeptide or functionally equivalent subsequence of (a) is having a sequence identity of at least 85% to (a) or (b), such as at least 90% to (a) or (b), for example at least 95% to (a) or (b), such as at least 97% to (a) or (b), for example at least 98% to (a) or (b), such as at least 99% to (a) or (b), where a polypeptide or functionally equivalent subsequence of (a)

In Examples 20 and 21 non-limiting examples of functional variants of DinQ ORF V are provided (SEQ ID NO: 19 to 22). The variants display activities comparable to the activity of the wild type DinQ ORF V.

The antibacterial polypeptide of the invention may be further adapted to facilitate the delivery of the polypeptide such as targeting to and uptake of the polypeptides in the target bacterium.

Accordingly, it may be advantageous to provide the polypeptide as a fusion polypeptide comprising the antibacterial polypeptide of the invention fused to a peptide that facilitates the uptake of the fusion peptide into the target bacteria. Thus, in one embodiment, the antibacterial polypeptide of the invention is fused to a further polypeptide which functions as a tag that promotes the uptake of the fusion polypeptide into bacteria.

Thus, in another embodiment, the antibacterial polypeptide of the invention is fused to a further polypeptide which functions as a tag that facilitates detection and or purification of the polypeptide (purification tag). A non-limiting example is provided with Example 6.

The Polynucleotides of the Invention

The inventors provide polynucleotides (nucleic acid) sequences encoding the antibacterial dinQ polypeptides of the invention. The sequences may be used for a wide range of applications. Non-limiting examples are recombinant expression of the antibacterial polypeptides such as for further isolation of the recombinant antibacterial polypeptides, or for recombinant expression in the host bacteria in order to inhibit the growth or kill said bacteria. Other non-limiting examples of the application of the polynucleotides of the invention are provided with Example 4 to 8. The person skilled in the art would know when to employ the DNA sequences such as the cDNA sequence encoding the polypeptide and when to employ the corresponding RNA sequences.

Accordingly, one aspect of the present invention relates to an isolated polynucleotide comprising a nucleic acid sequence encoding an antibacterial polypeptide of the invention.

In one embodiment, the isolated polynucleotide encoding an antibacterial polypeptide of the invention comprising a nucleic acid sequence selected from the group consisting of (a) SEQ ID NO:2 (DinQ ORF-I CDS DNA sequence), SEQ ID NO:4 (DinQ ORF-II CDS DNA sequence), SEQ ID NO:6 (DinQ ORF-III CDS DNA sequence), SEQ ID NO:8 (DinQ ORF-IV CDS DNA sequence), and SEQ ID NO:10 (DinQ ORF-V CDS DNA sequence), (b) a nucleic acid sequence with a sequence identity of at least 85% to (a) and encoding a functionally equivalent polypeptide.

Examples of functionally equivalent polypeptides are provided with the peptide set forth in SEQ ID NO: 19 to 22. It follows that any polynucleotide comprising nucleic acid sequence encoding a peptide selected from the list consisting of SEQ ID NO:19, SEQ ID NO:20, SEQ ID NO:21 and SEQ ID NO:22 also an embodiment of the present invention. In line with this, in one embodiment of the present invention the nucleic acid sequence is SEQ ID NO:10 (DinQ ORF-V CDS DNA sequence), where the start codon (GTG) is substituted the with a ATG start codon. In one embodiment, the isolated polynucleotide limited or essentially limited to the cited coding sequences (CDS).

In one embodiment, the polynucleotide comprises a nucleic acid sequence encoding an antibacterial polypeptide with the proviso that said polynucleotide does not encode SEQ ID NO:3 (DinQ ORF-I peptide).

In another embodiment, said isolated polynucleotide is a molecule of RNA. It follows that the cited SEQ IDs are provided in the DNA format corresponding to the complementary DNA of said RNA. Accordingly, in one embodiment the SEQ IDs of the invention refers to the DNA sequences and in another embodiment the SEQ IDs are used to refer to the corresponding RNA sequences.

In another embodiment, the nucleic acid sequence of (b) is selected from the group consisting of a nucleic acid sequence having at least 90% sequence identity to (a) and encoding a functionally equivalent polypeptide, a nucleic acid sequence having at least 95% sequence identity to (a) and encoding a functionally equivalent polypeptide, a nucleic acid sequence having at least 97% sequence identity to (a) and encoding a functionally equivalent polypeptide, a nucleic acid sequence having at least 98% sequence identity to (a) and encoding a functionally equivalent polypeptide, a nucleic acid sequence having at least 99% sequence identity to (a) and encoding a functionally equivalent polypeptide.

The inventors disclose the presence of four native dinQ transcripts that encodes the antibacterial polypeptides of the invention. The transcript are referred to as dinQ-a (corresponding DNA sequence is SEQ ID NO: 14), dinQ-b (corresponding DNA sequence is SEQ ID NO: 15), dinQ-c, and dinQ-d (corresponding DNA sequence is SEQ ID NO: 16). For further details see FIG. 2 and Example 2.

The dinQ-b (SEQ ID NO:15) is the most abundant of the dinQ transcripts in the agrB mutant genetic background and produces a highly toxic peptide of 27 amino acids (SEQ ID NO:11). Data from Northern blots, primer extension and in vitro transcription/translation analysis, performed by the inventors, demonstrate that translation is only detectable from the dinQ-b transcript. Further analysis of the primary sequence of dinQ-b (SEQ ID NO:15) shows that a Shine-Delgarno sequence is present in the primary sequence around the initiator GTG.

In another embodiment, the isolated polynucleotide is selected from the group consisting of SEQ ID NO: 14 (DinQ full length transcript, DinQ-a), SEQ ID NO: 15 (DinQ-b transcript), and SEQ ID NO: 16 (DinQ-d transcript).

In yet another embodiment, the isolated polynucleotide is selected from the group consisting of SEQ ID NO: 14 (DinQ full length transcript, DinQ-a), SEQ ID NO: 15 (DinQ-b transcript), SEQ ID NO: 16 (DinQ-d transcript), SEQ ID NO:2 (DinQ ORF-I CDS DNA sequence) SEQ ID NO:4 (DinQ ORF-II CDS DNA sequence), SEQ ID NO:6 (DinQ ORF-III CDS DNA sequence), SEQ ID NO:8 (DinQ ORF-IV CDS DNA sequence), and SEQ ID NO:10 (DinQ ORF-V CDS DNA sequence). In a further embodiment, the isolated polynucleotides is essentially a polynucleotide selected from the group consisting of SEQ ID NO: 14 (DinQ full length transcript, DinQ-a), SEQ ID NO: 15 (DinQ-b transcript), SEQ ID NO: 16 (DinQ-d transcript), SEQ ID NO:2 (DinQ ORF-I CDS DNA sequence) SEQ ID NO:4 (DinQ ORF-II CDS DNA sequence), SEQ ID NO:6 (DinQ ORF-III CDS DNA sequence), SEQ ID NO:8 (DinQ ORF-IV CDS DNA sequence), and SEQ ID NO:10 (DinQ ORF-V CDS DNA sequence).

AgrA and agrB

The arsR-gor intergenic region contain two small RNAs, agrA and agrB, which are transcribed in the opposite direction to dinQ The inventors provide two small 85 nt RNAs, agrA and agrB with antisense homology to the dinQ gene. The agrB mutant is sensitive to UV irradiation, whereas the agrA and dinQ single mutants showed no sensitivity. The deletion of dinQ in the agrB background relieved the UV sensitivity of the agrB single mutant, suggesting that enhanced levels of the dinQ transcript due to deficient RNA interference increase UV sensitivity of the agrB single mutant. Moreover, overexpressing the dinQ gene in wild type cells increases UV-sensitivity, supporting that constitutive expression of dinQ modulates (antagonizes) the cellular protection to UV exposure.

The polynucleotide set forth by the SEQ ID NO:12 (agrA encoding sequences) and SEQ ID NO:13 (agrB encoding sequences) of the present invention encodes non-coding RNAs.

One aspect of the invention relates to a method for reducing the load of or inhibition of propagation of a bacterium by increasing the activity (e.g. increasing the intracellular concentration) of a antibacterial peptide encoded by SEQ ID NO:1 (dinQ gene sequence) in said bacterium.

In one embodiment, the method for reducing the load of or inhibition of propagation of a bacterium is performed in vitro.

The inventors provide data that shows that agrB regulates dinQ expression (FIG. 3B and Example 10). The dinQ activity (e.g. the intracellular concentration of DinQ polypeptide) is increased in an agrB mutant background.

Accordingly, in one embodiment the method for reducing the load of or inhibition of propagation of a bacterium by increasing the activity (e.g. increasing the intracellular concentration) of a antibacterial peptide encoded by SEQ ID NO:1 (dinQ gene sequence) in said bacterium comprises a step of decreasing the activity (e.g intracellular concentration) of SEQ ID NO:13 (agrB) in said bacterium.

A nucleic acid sequence decreasing the activity of agrB (e.g intracellular concentration of agrB) described herein may e.g. interact with and destabilize the agrB RNA, stimulate ribonucleases degradation of agrB and thereby reduce the agrB mediated degradation of the dinQ transcripts.

Polynucleotides capable of a decreasing the activity of agrB (e.g intracellular concentration of agrB) may be provided as transcripts generated by heterologous expression of the corresponding cDNAs inserted into an expression cassette suitable for transcription in a host, such as but not limited to a vector selected from the group consisting of plasmids and phages.

The polynucleotides capable of decreasing the activity of agrB may also be generated by "in vitro transcription", which may be purified by means available to the skilled addressee.

In one embodiment, the polynucleotides capable of decreasing the activity of agrB (e.g intracellular concentration of agrB) is the complementary DNA (cDNA) of the transcript. These cDNAs may be in a truncated form of the parent cDNA maintaining the function of the full length cDNA or exhibiting activities exceeding the activity of the cDNA or corresponding transcript.

In a preferred embodiment, increasing the activity of dinQ RNA (e.g intracellular concentration of dinQ RNA) comprises decreasing the activity of agrB RNA (e.g intracellular concentration of agrB RNA) by antisense inhibition using an antisense oligonucleotide that comprises at stretch of complementary nucleotides of at least 20. Thus, the antisense oligonucleotide has a region of complementarity to the agrB RNA of at least 20 nucleotides. In another embodiment, the region of complementarity is selected from the group consisting of at least 10 nucleotides, at least 12 nucleotides, at least 14 nucleotides, at least 16 nucleotides and at least 18 nucleotides.

In one embodiment, the antisense molecule is a cationic phosphorodiamidate mopholino oligomers or protein nucleic acid. The oligomer is designed to target a relevant sequence within the bacterial genome of said bacteria. This method could be used to target the sRNA, agrB, and thus knock down the expression of agrB, which then lead to an elevated concentration of dinQ.

The sRNAs in themselves are modulators of protein and RNA expression within bacteria. The mechanisms that underly sRNA activity, for example sRNAs in combination with RNase E/Hfq could be used to regulate the effects of agrB.

Accordingly, in one embodiment the method for reducing the load of or inhibition of propagation of a bacterium comprising a step of decreasing the activity (e.g concentration) of SEQ ID NO:13 (agrB) in said bacterium using a peptide nucleic acid (PNA) oligomer, mopholino oligomers, LNA oligomer or any other suitable oligomer characterised in that the sequence of said oligomer is antisense to a sequences comprised in agrB.

It should be understood that any feature and/or aspect discussed in connection with the implementation of antisense molecules apply by analogy to heterologous expression using a vector or a phage expressing these antisense molecules for methods of the invention and preparation of the medicaments of the invention.

The Application of the Polypeptides

The antibacterial polypeptides of the invention provided by the inventors may be useful in the treatment of bacterial infections. The inventors disclose that the antibacterial DinQ polypeptides display toxic properties upon in vivo expression (Example 10). The inventors further provide that agrB negatively regulates dinQ expression (Example 10). Thus by decreasing the activity (e.g. concentration) of agrB in the bacteria, dinQ expression is subsequently up-regulated.

The antibacterial DinQ polypeptides of the present invention are therefore provided as new antibiotics, novel therapeutic strategies and approaches to combat the bacteria, in particular pathogenic bacteria that pose a serious threat to human health, such as antibiotic resistant bacteria.

Accordingly, one aspect of the present invention provides an antibacterial DinQ polypeptide for use as a medicament, in particular, for use in the treatment of a bacterial infection. Thus, the antibacterial dinQ polypeptide may be used in the manufacturing of a medicament for the treatment of a bacterial infection.

The inventors discovered that the DinQ polypeptides caused depolarization and ATP depletion of in the bacteria (Example 7 and 8). The DinQ polypeptides of the invention may therefore be used to increase the sensitivity of a bacterium to another antibiotic. The antibacterial DinQ polypeptides may therefore be useful in adjunctive treatment of bacterial infections.

In one embodiment the medicament is for adjunctive treatment of a bacterial infection. In a second embodiment the bacterial infection comprises at least one bacteria resistant to a least one antibiotic.

In a further aspect of the present invention the inventors provide a method for reducing the load of or inhibition of propagation of a bacterium by increasing the activity (e.g. concentration) of an antibacterial peptide encoded by SEQ ID NO:1 (dinQ gene sequence) in said bacterium.

In one embodiment the method comprises the introduction of a polypeptide in said bacterium, wherein said polypeptide is selected from the group consisting of
(a) a polypeptide encoded by SEQ ID NO:1 (dinQ gene sequence),
(b) a functionally equivalent subsequence of (a) of at least 15 amino acids
(c) a functionally equivalent polypeptide with a sequence identity of at least 85% to (a) or (b).

In a second embodiment the polypeptide is encoded by a polynucleotide sequence selected from the group consisting of SEQ ID NO: 14 (dinQ full length transcript, dinQ-a), SEQ ID NO: 15 (dinQ-b transcript), and SEQ ID NO: 16 (dinQ-d transcript).

In a third embodiment the polypeptide is selected from the list consisting of SEQ ID NO:3 (DinQ ORF-I peptide), SEQ ID NO:5 (DinQ ORF-II peptide), SEQ ID NO:7 (DinQ ORF-III peptide), SEQ ID NO:9 (DinQ ORF-IV peptide), SEQ ID NO:11 (DinQ ORF-V peptide) and SEQ ID NO:17 (DinQ ORF-V peptide with N-tem Met).

In yet another embodiment, the polypeptide has the amino acid sequence set forth by SEQ ID NO:5 (DinQ ORF-II peptide). In one embodiment, the polypeptide has the amino acid sequence set forth by SEQ ID NO:9 (DinQ ORF-IV peptide). In a particular embodiment, the polypeptide has the amino acid sequence set forth by SEQ ID NO:11 (DinQ ORF-V peptide).

In one embodiment, the method for reducing the load of or inhibition of propagation of a bacterium is performed in vitro.

Thus, one embodiment provides an in vitro method for reducing the load of or inhibition of propagation of a bacterium, comprising introducing a polypeptide in said bacterium, wherein said polypeptide is selected from the group consisting of (a) a polypeptide encoded by SEQ ID NO:1 (dinQ gene sequence) selected from the list consisting of SEQ ID NO:17 (DinQ ORF-V peptide with N-tem Met), SEQ ID NO:5 (DinQ ORF-II peptide), SEQ ID NO:7 (DinQ ORF-III peptide), SEQ ID NO:9 (DinQ ORF-IV peptide), and SEQ ID NO:11 (DinQ ORF-V peptide), (b) a functionally equivalent subsequence of (a) of at least 15 amino acids (c) a functionally equivalent polypeptide with a sequence identity of at least 85% to (a) or (b).

In one embodiment, the functionally equivalent polypeptide is selected from the group consisting of SEQ ID NO:19 (G10K variant of DinQ ORF-V peptide), SEQ ID NO:20 (L23I variant of DinQ ORF-V peptide), SEQ ID NO:21 (I7V variant of DinQ ORF-V peptide), and SEQ ID NO:22 (L12I, I13V double mutant variant of DinQ ORF-V peptide).

As discussed the antibacterial polypeptides may be used in an adjunctive therapy with commonly used antibiotic. Accordingly, the method further comprises the administration of an antibiotic. In one embodiment, the method further comprises the administration of an inhibitor of the SOS response.

In a particular embodiment, the method for reducing the load of or inhibition of propagation of a bacterium comprising increasing the activity (e.g. concentration) of an antibacterial peptide by introducing the polypeptide into the said bacterium using a vector adapted for expression of said polypeptide.

The antibacterial dinQ polypeptides of the invention provided by the inventors may be useful in the treatment of bacterial infections as well as reducing bacterial contamination of food and feed. The antibacterial polypeptides may be provided as isolated or synthetic polypeptides or delivered as a vector adapted for expression of said polypeptides. The polypeptides or vectors encoding the same may be formulated such as in a pharmaceutical composition comprising a suitable carrier for the specific application. Accordingly, one embodiment of the present invention provides a pharmaceutical composition comprising at least one polypeptide or polynucleotide of the invention and at least one pharmaceutical acceptable carrier.

One aspect of the present invention relates to the use of an antibacterial DinQ polypeptide of the invention or polynucleotide encoding an antibacterial DinQ polypeptide of the invention for reducing the load of or inhibiting the propagation of a bacterium. In one embodiment, the polynucleotide is for in vitro use.

In a particular embodiment, the antibacterial DinQ polypeptide of the invention or polynucleotide encoding an antibacterial DinQ polypeptide of the invention, polynucleotide or vector encoding the same are used in combination with a least one antibiotic.

Transcriptional Inducers and Repression of agrB

Transcriptional inducers may also be used to induce expression of endogenous DinQ polypeptides. Induction of endogenous DinQ polypeptides may be accomplished by targeting the regulators of dinQ such as agrB.

In one embodiment, the method for reducing the load of or inhibition of propagation of a bacterium by increasing the activity (e.g. the concentration) of an antibacterial DinQ polypeptide comprises a step of introducing a nucleic acid sequence, which decreases the activity (e.g. the concentration) of agrB in the bacterium.

In a further embodiment, the nucleic acid sequence decreasing the activity of agrB in the bacterium is an oligonucleotides comprising at least one RNA monomer, DNA monomer, LNA monomer, PNA monomer or any other suitable monomer.

In one embodiment, the oligonucleotide is built from RNA monomers. In another preferred embodiment, the oligonucleotide is synthesized from DNA monomers.

The nucleic acid sequence decreasing the activity (e.g. the concentration) of agrB in the bacterium may be used in the preparation of a medicament for treatment of a bacterial infection accordingly.

Heterologous expression of the nucleic acid sequence decreasing the activity (e.g. the concentration) of agrB is an alternative to the introduction of exogenously synthesized oligonucleotides into the bacterium, the activity (e.g. the concentration) of agrB may be reduced by delivering a gene encoding a RNA into the bacterium.

The nucleic acid sequence decreasing the activity (e.g. the concentration) of agrB described herein may e.g. interact with and destabilize the agrB RNA and stimulate ribonucleases degradation of agrB.

Oligonucleotides may be synthesised either by enzymatic syntheses e.g. using T7 RNA polymerase or by standard chemistry. RNA and DNA oligonucleotides are offered by many providers.

Alternatively, the nucleic acid sequence decreasing the activity (e.g. the concentration) of agrB may bind to the corresponding region of the dinQ transcripts and prevent agrB mediated degradation.

The Application of the Polynucleotides

The polynucleotides of the invention encoding the DinQ antibacterial polypeptides or a polynucleotide encoding an activity decreasing the activity of agrB (anti-agrB activity) may be inserted in a vector such as a vector adapted for the expression of said DinQ antibacterial polypeptides or anti-agrB activity. The vectors may be used for amplification of the polynucleotides (RNA and/or DNA) of the invention and/or expression of the antibacterial polypeptides. Thus, in one embodiment of the present invention, the vector is a phage vector adapted for expression of said polypeptide or anti-agr activity (polynucleotide/polypeptide).

Vector

Thus one aspect concerns a vector comprising a nucleic acid sequence encoding an antibacterial polypeptide of the invention. Another embodiment, concerns a vector comprising a nucleic acid sequence encoding an activity (an anti-agrB activity) that decreases the activity of agrB (e.g. the concentration). It follows that the vectors preferably are adapted to expressing of said nucleic acid sequence in the target bacterium.

In another embodiment, the vector is adapted for expression of said antibacterial polypeptide or a polynucleotide encoding an activity that decreases the activity (e.g. the concentration) of agrB.

The polynucleotides of the present invention are typically subcloned in expression vectors such as a plasmid or phage vector adapted for expression in the target host cell in question. The vector may be any known vector, which suits the present application. Typically such expression vector comprises multiple cloning sites in an expression cassette for insertion of the polynucleotides (DNA insert) in question such as polynucleotides comprising a nucleic acid sequence encoding an antibacterial dinQ polypeptide or an anti-agrB activity of the invention. The cloning sites of the expression vector is usually positioned downstream of an expression control sequence capable of directing transcription of the DNA insert. The expression control sequence (or promoter) may comprise a wide range of promoter elements such as elements, which enables either constitutive or conditional expression of the inserted polynucleotide. A conditional (inducible) promoter may comprise DNA elements binding transcriptions factors or repressor, which are regulated by the environmental conditions (e.g. temperature, pH) or the presence/absence of a ligand such as IPTG. An non-limiting example of IPTG mediated induction of dinQ polypeptides of the invention are provided in Example 5 to 8. The transcription may also be switch on (or off) by a site-specific recombinase (e.g Cre or FLP) exciting a DNA element of the vector blocking the transcription and formation of a functional transcript encoding the polypeptide or a non-coding RNA of the invention.

The expression control sequence of the vector controls and regulates the nucleic acid sequence encoding the antibacterial polypeptide or anti-agrB activity of the vector to which it is operatively linked.

Thus in one embodiment, the nucleic acid sequence encoding the antibacterial polypeptide or anti-agrB activity of the vector is operatively linked to an expression control sequence (promoter). In another embodiment, the expression control sequence is an inducible promoter such as IPTG inducible.

In another embodiment the vector comprises a nucleic acid sequence encoding an antibacterial polypeptide of the invention selected from the list consisting of (a) a polypeptide encoded by SEQ ID NO:1 (dinQ gene sequence), (b) a functionally equivalent subsequence of (a) of at least 15 amino acids (c) a polypeptide or functionally equivalent polypeptide with a sequence identity of at least 85% to (a) or (b).

In a third embodiment, said a polypeptide or functionally equivalent subsequence of (a) is having a sequence identity of at least 85% to (a) or (b), such as at least 90% to (a) or (b), for example at least 95% to (a) or (b), such as at least 97% to (a) or (b), for example at least 98% to (a) or (b), such as at least 99% to (a) or (b).

In a fourth embodiment, said subsequence is having at least the length of 15 amino acids (aa.), is at least 20 aa., for example at least 25 aa., such as at least 30 aa., for example at least 35 aa., such as at least 40 aa., for example at least 45 amino acids.

In a further embodiment, the vector comprises a nucleic acid sequence selected from the group consisting SEQ ID NO: 14 (dinQ full length transcript, dinQ-a), SEQ ID NO: 15 (dinQ-b transcript), SEQ ID NO: 16 (dinQ-d transcript), SEQ ID NO:2 (DinQ ORF-I CDS DNA sequence) SEQ ID NO:4 (DinQ ORF-II CDS DNA sequence), SEQ ID NO:6 (DinQ ORF-III CDS DNA sequence), SEQ ID NO:8 (DinQ ORF-IV CDS DNA sequence), and SEQ ID NO:10 (DinQ ORF-V CDS DNA sequence).

In yet a further embodiment, the vector comprises a nucleic acid sequence encoding an antibacterial polypeptide with the proviso that said nucleic acid sequence and said vector does not encode SEQ ID NO:3 (DinQ ORF-I peptide).

In one embodiment, the vector comprises the nucleic acid sequence is set forth by SEQ ID NO:4 (DinQ ORF-II CDS DNA sequence). In second embodiment, the vector is comprising the nucleic acid sequence set forth by SEQ ID NO:6 (DinQ ORF-III CDS DNA sequence). In one embodiment, the vector comprises the nucleic acid sequence set forth by SEQ ID NO:8 (DinQ ORF-IV CDS DNA sequence). In one embodiment, the vector comprises the nucleic acid sequence set forth by SEQ ID NO:10 (DinQ ORF-V CDS DNA sequence). In one embodiment, the vector comprises a nucleic acid sequence encoding the polypeptide having the amino acids sequence set forth by SEQ ID NO:17.

In another embodiment, the functionally equivalent polypeptide is selected from the group consisting of SEQ ID NO:19 (G10K variant of DinQ ORF-V peptide), SEQ ID NO:20 (L23I variant of DinQ ORF-V peptide), SEQ ID NO:21 (I7V variant of DinQ ORF-V peptide), and SEQ ID NO:22 (L12I, I13V double mutant variant of DinQ ORF-V peptide).

Phage Vector

A bacteriophage is any one of a number of viruses that infect bacteria and thus an excellent tool to enter a host cell. In order to efficiently deliver the polynucleotide encoding the antibacterial DinQ polypeptides of the invention to the target it may be advantageous to employ a bacteriophage vector.

Thus, applying this to the capabilities of the polypeptides of the invention and/or the polynucleotide described herein, a phage adapted for expression of polypeptides and/or a polynucleotide of the invention may be used in the preparation of a medicament for the use in the treatment of bacterial infections (phage therapy).

The phages functions as a vector for delivery of the antibacterial DinQ polypeptides, anti-agrB activity, or antisense by heterologous expression from an expression cassette inserted in the genome of the phage. Transcription from the expression cassette may either by constitutive or inducible (conditional).

In one embodiment of the present invention, the vector is a phage.

Applying the properties of the phage vector to the capabilities of the antibacterial DinQ polypeptides and anti-agrB activity described herein, a phages adapted for expression of an antibacterial dinQ polypeptide and/or anti-agrB activity may be used for phage therapy application in the treatment of a bacterial infection. Any phage strain suitable for delivering the antibacterial DinQ polypeptides and/or anti-agrB activity to the target bacteria (or other pathogens) is contemplated as useful in the present invention. Included are lytic as well as lysogenic phages.

The phage vector adapted for expression of an antibacterial DinQ polypeptide and/or anti-agrB activity may be amplified and isolated by any suitable methods known by the skilled person.

Accordingly, the isolated phage vector may be used in the preparation of a medicament for the treatment of a bacterial infection.

Thus, one aspect of the present concerns a vector (such as a bacteriophage) encoding and adapted for expression of an antibacterial DinQ polypeptide and/or anti-agrB activity of the invention for use as a medicament for the treatment of a bacterial infection.

The phages useful in the preparation of a medicament for the treatment of a bacterial infection may encode any of the disclosed antibacterial dinQ polypeptide or anti-agrB activity of the invention.

In one embodiment the medicament comprising the phage are provided as an adjunct to or as a replacement for those antibiotics that are no longer functioning in a bacteriostatic or bactericidal manner due to the development of drug resistance.

Another embodiment relates to a medicament comprising the phage for the treatment of bacterial infections in subjects who are allergic to the antibiotics that would otherwise be indicated.

One advantage of phage therapy is that it has fewer side effects than many of the antibiotics and/or chemotherapeutic drugs that would otherwise be indicated for the infection in question.

Phage therapy may be combined with lytic bacteriophages to treat pathogenic bacterial infections. In a particular embodiment, the phage vector of the present invention posses both properties of heterologous expression of an antibacterial DinQ polypeptide (and/or anti-agrB activity) and bacterial lysis.

The phage therapy may be applied as a stand-alone treatment or adjunctive treatment. Use of the phage according to the invention as adjunctive therapy comprise use with other phages such as purely lytic phages or other therapeutics.

The phage therapy of the invention may be adapted to application for a large spectrum of target bacteria and bacterial infections by selection of phages that are specific for each of the bacterial strains of interest. Selection may be performed by means of genetic engineering or selection by serial passages. Phages may also be adapted to avoid or delay the immune response of the subject in the need of treatment in order to increase the time of clearance of circulating phages from the subject.

Bacteriophage preparations and compositions of the invention may be administered to the human or animal patient topically, systemically, orally, or by some other means suitable for delivering an effective dose to the site of the infection to be treated. Bacteriophage administration will be in such a way that the bacteriophage can be incorporated into bacteria at the site of infection. The routes of administration and dosages described are intended only as a guide since a skilled practitioner will be able to determine the optimum route of administration and dosage for any particular patient and condition. Routes of administration comprise oral, pulmonary (by aerosol or by other respiratory device for respiratory tract infections), nasal, IV, IP, per vagina, per rectum, intra-ocular, by lumbar puncture, intrathecal, and by burr hole or craniotomy if need be for direct insertion onto the meninges (e.g. in a heavily thickened and rapidly fatal tuberculous meningitis). The medicaments comprising the phage may be formulated accordingly.

Any phage could be used as a delivery vehicle. In order to function some modification may be needed in order to work correctly. Modification would involve alteration of the packaging pathway of viral DNA/RNA so that the DNA/RNA encoding dinQ would be packed in the place of the viral DNA/RNA. In addition phage that work via lysis may have to have that lysis function deactivated.

In one embodiment the phage vector system is based on Caudovirales, Inoviridae, Inovirus, or Enterobacteria phage M13. In one embodiment, the page is not a lytic phage. In one embodiment, the phage is an inophage. The inophage only need to be modified so that they package foreign DNA.

Several phage derived vector systems may be applied to in the present invention, such as but not limited to M13, λ phage, P22, T4, SP01-phage and IRA. In one embodiment, the vector is a M13 phagemid derived vector.

In one embodiment the phage comprises a nucleic acid sequence encoding an antibacterial polypeptide of the invention selected from the list consisting of
 (a) a polypeptide encoded by SEQ ID NO:1 (dinQ gene sequence),
 (b) a functionally equivalent subsequence of (a) of at least 15 amino acids
 (c) a functionally equivalent polypeptide with a sequence identity of at least 85% to (a) or (b).

In a further embodiment, the nucleic acid sequence is selected from the group consisting SEQ ID NO: 14 (dinQ full length transcript, DinQ-a), SEQ ID NO: 15 (dinQ-b transcript), SEQ ID NO: 16 (dinQ-d transcript), SEQ ID NO:2 (DinQ ORF-I CDS DNA sequence) SEQ ID NO:4 (DinQ ORF-II CDS DNA sequence), SEQ ID NO:6 (DinQ ORF-III CDS DNA sequence), SEQ ID NO:8 (DinQ ORF-IV CDS DNA sequence), and SEQ ID NO:10 (DinQ ORF-V CDS DNA sequence). In one embodiment, the vector comprises a nucleic acid sequence encoding the polypeptide having the amino acids sequence set forth by SEQ ID NO:17.

In another embodiment, the functionally equivalent polypeptide is selected from the group consisting of SEQ ID NO:19 (G10K variant of DinQ ORF-V peptide), SEQ ID NO:20 (L23I variant of DinQ ORF-V peptide), SEQ ID NO:21 (I7V variant of DinQ ORF-V peptide), and SEQ ID NO:22 (L12I, I13V double mutant variant of DinQ ORF-V peptide).

The phage is adapted for expression of the nucleic acid sequence encoding an antibacterial polypeptide of the invention in the target bacteria.

The antibacterial dinQ polypeptide can be constitutively expressed from the vector (e.g. phage) or conditionally expressed using a regulator of expression e.g use an inducer like IPTG or any other suitable ligand where expression is regulated by the presence or absence of the regulator.

In Vitro—In Vivo Validation and Screening of Phages of the Invention

A potentially useful method of screening and further developing peptides (or polynucleotides) of the invention for enhanced therapeutic efficacy may involve screening a phage-displayed peptide (or polynucleotide) library in an in vitro system. A pathogenic bacterial strain (e.g an *E. coli* strain such as *E. coli* (ER2738)) may be used a host for the phage library for expression of said peptides or polynucleotides. Preferably the expression of said peptides or polynucleotides is under control of a conditional promoter such as an IPTG inducible promoter. Expression may then be induced in the host cells of the phage library. Subsequently, phages may be isolated from any surviving host cells, which may be used to extract phages encoding low efficacy peptides/polynucleotides from the parent library (or from a controls host cells comprising the same library but not subjected to transcriptional induction). The system may be used to maturate the peptides (or polynucleotides) of the invention for enhanced therapeutic efficacy going to rounds of infection and induction. The system may also me used to identify the best candidates to target a specific pathogenic bacterium.

To test the therapeutic potential of the antibacterial polypeptides of the present invention or polynucleotides of the invention, the animal model may be employed such as but not limited to a neutropenic murine thigh infection model and the pathogenic bacterial strain such as an *E. coli* strain such as *E. coli* (ER2738) (ATCC 259222). The animal model may be infected with a pathogenic (e.g. *E. coli* strain) comprising an inducible (such as IPTG inducible) expression vector of the invention (preferably a phage vector) adapted for expression of the antibacterial polypeptides of the present invention or polynucleotides of the invention under control of the inducible promoter. Following the infection of the animals, expression of the antibacterial polypeptides of the present invention or polynucleotides of the invention may be induced such as by adding the appropriate ligand to the drinking water. The infected animals may be at regular intervals such as 24, 48 and 72 h after the infection and subjected to further analysis. Thigh tissue may be isolated and subsequently homogenized, diluted and plated on media (eventually with and without antibiotics) to quantify the number of viable (and resistant) strains.

Food and Feed Applications

The present invention also relates to methods and compositions for the treatment of bacterial contamination of food by the use of a phage adapted for expression of an antibacterial polypeptide and/or anti-agrB activity as described in the present herein, preferably blended with an appropriate carrier. The method for treating food stuffs comprises treating the food stuffs with such an agent comprising an effective amount of the means for reversal of the antibiotic resistance or as direct treatment.

Such means may be used to treat or prevent bacterial contamination of foodstuffs. Feed for livestock, poultry and beef in slaughterhouses, canned and bottled goods, salad bars, and eggs are just some of the food items that can be treated with these phages of the present invention to reduce the risk of food contamination by bacteria. The phages of the present invention can be applied along the entire food processing chain in place of or in combination with antibiotics to prevent dangerous infectious bacteria from growing where antibiotics have not, or cannot, be used.

Accordingly, the present invention provides a vector (such as a phage) adapted for expression of an antibacterial polypeptide and/or anti-agrB activity of the invention for reducing the load of contaminating bacteria in food and/or feed products.

Thus, in one embodiment the polypeptide or vector of the invention is used for reducing the load of or inhibiting the propagation of a bacterium in vitro.

The Conditions Subjected to the Use of the Polypeptides/Polynucleotides

One aspect of the invention concerns, a pharmaceutical composition comprising an antibacterial polypeptide of the present invention, or
a polynucleotide encoding an antibacterial polypeptide of the present invention, and
at least one pharmaceutically acceptable additive.

In one embodiment, the polynucleotide is provided in the form of a vector of the present invention.

The pharmaceutical composition is useful for combating bacterial infections range from mild infections to severe infections such as sepsis. The pharmaceutical composition may be for a stand-alone treatment of the bacterial infection or for use in an in combination with a least one other antibiotic.

In a further embodiment, the pharmaceutical composition comprising an antibacterial polypeptide of the present invention, or a polynucleotide encoding an antibacterial polypeptide of the present invention is administered to the patient in the need thereof prior to the treatment with said other antibiotic.

In a further embodiment, the at least one pharmaceutically acceptable additive is selected from the group consisting of proteins, carbohydrates, sugar, magnesium state, cellulose, talc, starch-gelatin paste, calcium carbonate, pharmaceutically acceptable carriers, excipients, diluents and solvents.

In one embodiment, the pharmaceutical composition which is in a form to be administered through an oral, intravenous, an inhalation, intramuscular or subcutaneous route. In another embodiment, the pharmaceutical composition which is in a form to be administered topically, such as for the treatment of an infected wound.

In one embodiment, said polynucleotide encoding is provided as vector adapted for expression of said antibacterial polypeptide in the bacteria. In one embodiment, the vector is a phage. Ways of configuring vectors are described herein by non-limiting examples. The skilled person is familiar with means of adapting vectors for delivery and expression of a transgene, such as a polynucleotide encoding an antibacterial polypeptide of the present, in a target bacterium.

In another embodiment, the antibacterial polypeptide is a polypeptide encoded by SEQ ID NO:1 (dinQ gene sequence). In a further embodiment, said polypeptide is selected from the group consisting of (a) a polypeptide encoded by SEQ ID NO:1 (dinQ gene sequence), (b) a functionally equivalent subsequence of (a) of at least 15 amino acids (c) a functionally equivalent polypeptide with a sequence identity of at least 85% to (a) or (b).

In one embodiment, the antibacterial polypeptide selected from the group consisting of SEQ ID NO:3 (DinQ ORF-I peptide), SEQ ID NO:5 (DinQ ORF-II peptide), SEQ ID NO:7 (DinQ ORF-III peptide), SEQ ID NO:9 (DinQ ORF-IV peptide), SEQ ID NO:11 (DinQ ORF-V peptide) and SEQ ID NO:17 (DinQ ORF-V peptide with N-tem Met). In a preferred embodiment, the antibacterial polypeptide SEQ ID NO:11 (DinQ ORF-V peptide).

In another embodiment, the functionally equivalent polypeptide is selected from the group consisting of SEQ ID NO:19 (G10K variant of DinQ ORF-V peptide), SEQ ID NO:20 (L23I variant of DinQ ORF-V peptide), SEQ ID NO:21 (I7V variant of DinQ ORF-V peptide), and SEQ ID NO:22 (L12I, I13V double mutant variant of DinQ ORF-V peptide).

In another preferred embodiment, the antibacterial peptide is encoded by a phage vector adapted for expression of the polypeptide in said bacterium.

A further aspect concerns a method of treating a bacterial infection in a subject (such as a human being in the need thereof), said method comprising the step of administering to said subject a pharmaceutical composition comprising an effective amount of an antibacterial polypeptide of the present invention.

Thus in one embodiment, said method comprising the step of administering to said subject the pharmaceutical composition of the present invention comprising an effective amount of an antibacterial polypeptide of the present invention or said vector of the present invention.

In another embodiment the method is an adjunctive treatment.

In one embodiment, the method of treating a bacterial infection in a subject comprises a further step of is administered to said subject in the need thereof an effective amount of at least one other antibiotic. In another embodiment, the pharmaceutical composition of the present invention is administered to said subject prior to the administered of the other antibiotic in order to sensitize the bacteria to said other antibiotic.

In a further embodiment, said least one other antibiotic is selected from the group consisting of: rifamycine, aminoglycosides, carbapenems, cephalosporins, cephems, glycopeptides, fluoroquinolones/quinolones, macrolides, oxazolidinones, penicillins, streptogramins, sulfonamides, and tetracyclines. Most preferably, the antibiotic is rifamycin or quinolone.

In yet a further embodiment, said at least one other antibiotic is selected from nucleic acid synthesis inhibitors such as nalidixic acid and mitomycin C, protein synthesis inhibitors such as tetracycline, cell wall inhibitors such as ampicillin, and metabolic inhibitors such as erythromycin.

One aspect concerns the use of a polypeptide antibacterial polypeptide of the invention or polynucleotide of the invention for reducing the load of or inhibiting the propagation of a bacterium. In one embodiment, said polypeptide is used in combination with a least one antibiotic.

In one embodiment, the polypeptide or vector of the invention is used for reducing the load of or inhibiting the propagation of a bacterium in vitro.

One embodiment concerns, a method for reducing the load of or inhibition of propagation of a bacterium is performed on an infected subject such as a mammal, said group of mammals not including humans. In another embodiment, the group of mammals does include humans.

In a further embodiment, the method for reducing the load of or inhibition of propagation of a bacterium is performed on an infected subject is also provided for the treatment of bacterial infections, where the subject in the need of treatment are allergic to the antibiotic that would otherwise be indicated.

Another embodiment the method for reducing the load of or inhibition of propagation of a bacterium, where the bacteria is resistant to at least one commonly used antibiotic.

As mentioned above, the polypeptides/polynucleotides or expression vectors encoding the same may be applied as a stand-alone treatment or adjunctive treatment.

DinQ Increase Sensitivity to Antibiotics

Figure 16:
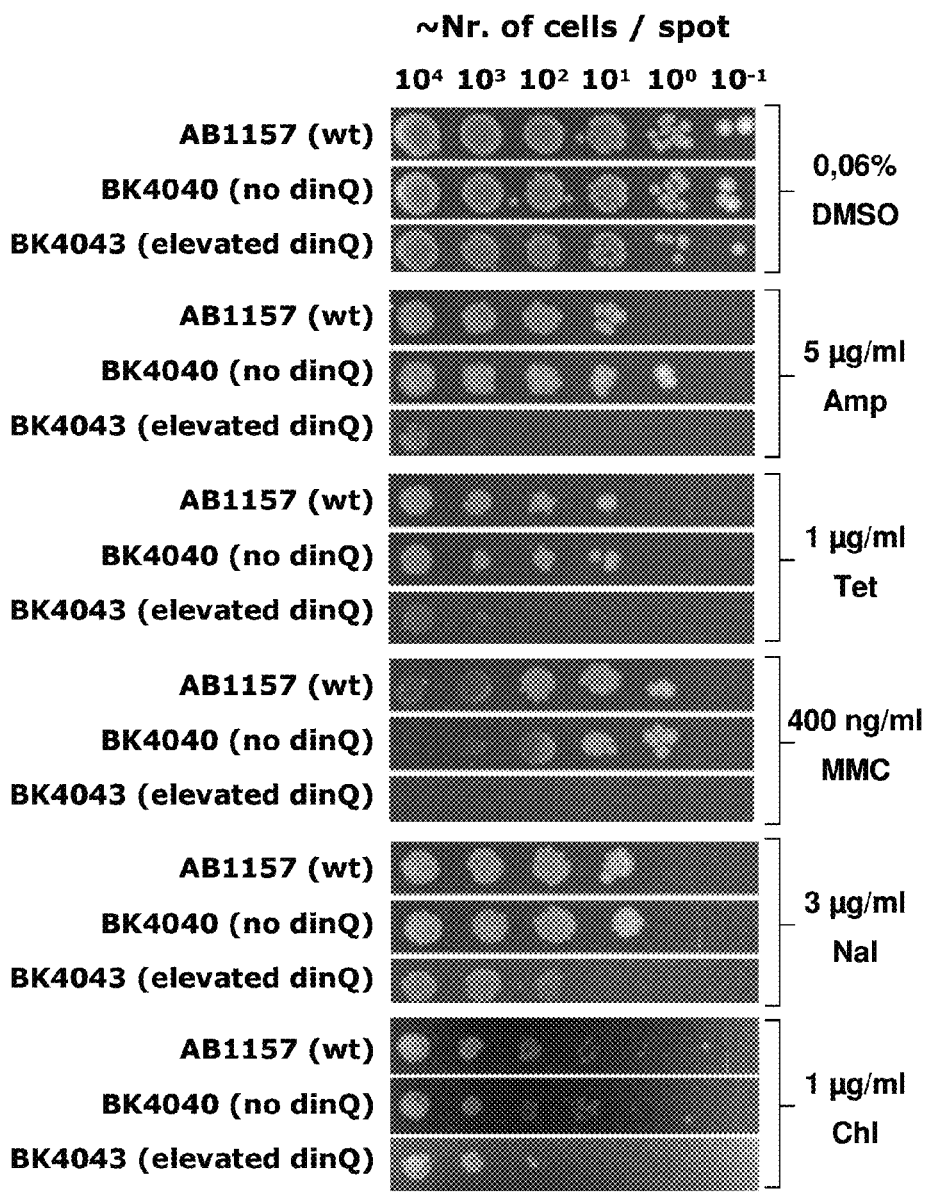

The inventors have discovered that bacteria displaying elevated DinQ expression display increased sensitivity to antibiotics used to combat bacterial infections. Various types of antibiotics such as nucleic acid synthesis inhibitors, (nalidixic acid, mitomycin C), protein synthesis inhibitors (tetracycline), cell wall inhibitors (ampicillin) and metabolic inhibitors (erythromycin) were tested in strains with elevated levels of DinQ or no DinQ expression. The inventors find that the *E. coli* mutant with elevated DinQ displayed increased sensitivity to all the antibiotics tested (FIG. 16 and Example 14). It thus appears that DinQ increases influx or inhibits efflux of antibiotics.

It is clear from the experimental data provided in Example 14 and presented in FIG. 16, that the effect of adjunctive treatment of bacterial infection may be synergistic. In particular if the infection is treated with the antibacterial polypeptides of the invention and subsequently treated with a antibiotic such as at least one of the commonly know antibiotics described herein.

Sepsis

Sepsis is a serious clinical condition in which infectious agents (e.g. bacteria) or products of infection (bacterial toxins) enter the blood, lungs, skin, or other tissues and profoundly affect body systems. Sepsis is characterized by a whole-body inflammatory state (referred to as systemic inflammatory response syndrome or SIRS) reflecting the presence of a known or suspected infection.

In the context of the present invention, the term "sepsis" refers to sepsis associated with an underlying bacterial infection.

A further aspect concerns a method of treating sepsis in a subject (such as a human being in the need thereof), said method comprising the step of administering to said subject a pharmaceutical composition comprising an effective amount of an antibacterial polypeptide of the present invention.

One embodiment of the present invention concerns the method for treating sepsis by increasing the activity of a antibacterial peptide encoded by SEQ ID NO:1 (dinQ gene sequence) in said bacterium.

In one embodiment, the method comprises introducing a polypeptide in said bacterium, wherein said polypeptide is selected from the group consisting of (a) a polypeptide encoded by SEQ ID NO:1 (dinQ gene sequence), (b) a functionally equivalent subsequence of (a) of at least 15 amino acids (c) a functionally equivalent polypeptide with a sequence identity of at least 85% to (a) or (b).

In one embodiment, the antibacterial polypeptide selected from the group consisting of SEQ ID NO:3 (DinQ ORF-I peptide), SEQ ID NO:5 (DinQ ORF-II peptide), SEQ ID NO:7 (DinQ ORF-III peptide), SEQ ID NO:9 (DinQ ORF-IV peptide), SEQ ID NO:11 (DinQ ORF-V peptide) and SEQ ID NO:17 (DinQ ORF-V peptide with N-tem Met).

In a preferred embodiment, the antibacterial polypeptide SEQ ID NO:11 (DinQ ORF-V peptide). In another preferred embodiment, the antibacterial polypeptide SEQ ID NO:17 (DinQ ORF-V peptide with N-tem Met)

In another embodiment, the functionally equivalent polypeptide is selected from the group consisting of SEQ ID NO:19 (G10K variant of DinQ ORF-V peptide), SEQ ID NO:20 (L23I variant of DinQ ORF-V peptide), SEQ ID NO:21 (I7V variant of DinQ ORF-V peptide), and SEQ ID NO:22 (L12I, I13V double mutant variant of DinQ ORF-V peptide).

In another preferred embodiment, the antibacterial peptide is encoded by vector such as a phage vector adapted for expression of the polypeptide in said bacterium. Accordingly, the antibacterial polypeptide is delivered to the patient in the form of a vector adapted for targeting the bacteria and expressing the antibacterial polypeptide in said bacteria.

One aspect of the invention concerns an antibacterial peptide of the present invention for use as a medicament.

In one embodiment, the antibacterial polypeptide selected from the group consisting of SEQ ID NO:3 (DinQ ORF-I peptide), SEQ ID NO:5 (DinQ ORF-II peptide), SEQ ID NO:7 (DinQ ORF-III peptide), SEQ ID NO:9 (DinQ ORF-IV peptide), SEQ ID NO:11 (DinQ ORF-V peptide) and SEQ ID NO:17 (DinQ ORF-V peptide with N-tem Met).

In another embodiment, the functionally equivalent polypeptide is selected from the group consisting of SEQ ID NO:19 (G10K variant of DinQ ORF-V peptide), SEQ ID NO:20 (L23I variant of DinQ ORF-V peptide), SEQ ID NO:21 (I7V variant of DinQ ORF-V peptide), and SEQ ID NO:22 (L12I, I13V double mutant variant of DinQ ORF-V peptide).

Another aspect of the present invention concerns an antibacterial peptide of the present invention for use in the treatment of a bacterial infection. Yet another aspect concerns the use of an antibacterial peptide of the present invention for the preparation of a medicament for the treatment of a bacterial infection. In one embodiment, the infection is an infected wound.

A further aspect of the present invention concerns an antibacterial peptide of the present invention for use in the treatment of sepsis. Yet a further aspect concerns the use of an antibacterial peptide of the present invention for the preparation of a medicament for the treatment of sepsis.

In one embodiment, the antibacterial polypeptide selected from the group consisting of SEQ ID NO:3 (DinQ ORF-I peptide), SEQ ID NO:5 (DinQ ORF-II peptide), SEQ ID NO:7 (DinQ ORF-III peptide), SEQ ID NO:9 (DinQ ORF-IV peptide), SEQ ID NO:11 (DinQ ORF-V peptide) and SEQ ID NO:17 (DinQ ORF-V peptide with N-tem Met).

In another embodiment, the functionally equivalent polypeptide is selected from the group consisting of SEQ ID NO:19 (G10K variant of DinQ ORF-V peptide), SEQ ID NO:20 (L23I variant of DinQ ORF-V peptide), SEQ ID NO:21 (I7V variant of DinQ ORF-V peptide), and SEQ ID NO:22 (L12I, I13V double mutant variant of DinQ ORF-V peptide).

In one embodiment, said antibacterial polypeptide is for adjunctive treatment.

In another embodiment, said antibacterial polypeptide is for use in combination with another antibiotic such as an antibiotic selected from the group consisting of: rifamycine, aminoglycosides, carbapenems, cephalosporins, cephems, glycopeptides, fluoroquinolones/quinolones, macrolides, oxazolidinones, penicillins, streptogramins, sulfonamides, tetracyclines, nalidixic acid, mitomycin C, ampicillin, and metabolic inhibitors such as erythromycin.

One aspect of the invention concerns a vector (such as a recombinant phage) encoding and adapted for expression an antibacterial peptide of the present invention for use as a medicament.

In one embodiment, the antibacterial polypeptide selected from the group consisting of SEQ ID NO:3 (DinQ ORF-I peptide), SEQ ID NO:5 (DinQ ORF-II peptide), SEQ ID NO:7 (DinQ ORF-III peptide), SEQ ID NO:9 (DinQ ORF-IV peptide), SEQ ID NO:11 (DinQ ORF-V peptide) and SEQ ID NO:17 (DinQ ORF-V peptide with N-tem Met).

In another embodiment, the functionally equivalent polypeptide is selected from the group consisting of SEQ ID NO:19 (G10K variant of DinQ ORF-V peptide), SEQ ID NO:20 (L23I variant of DinQ ORF-V peptide), SEQ ID NO:21 (I7V variant of DinQ ORF-V peptide), and SEQ ID NO:22 (L12I, I13V double mutant variant of DinQ ORF-V peptide).

One aspect of the present invention concerns a vector (such as a recombinant phage) encoding and adapted for expression an antibacterial peptide of the present invention for use in the treatment of a bacterial infection. Another aspect concerns the use of a vector (such as a recombinant phage) encoding and adapted for expression an antibacterial peptide of the present invention for the preparation of a medicament for the treatment of a bacterial infection.

In one embodiment, said vector (such as a recombinant phage) is for adjunctive treatment.

In another embodiment, said vector (such as a recombinant phage) is for use in combination with another antibiotic such as an antibiotic selected from the group consisting of: rifamycine, aminoglycosides, carbapenems, cephalosporins, cephems, glycopeptides, fluoroquinolones/quinolones, macrolides, oxazolidinones, penicillins, streptogramins, sulfonamides, tetracyclines, nalidixic acid, mitomycin C, ampicillin, and metabolic inhibitors such as erythromycin.

A further aspect of the present invention concerns a vector (such as a recombinant phage) encoding and adapted for expression an antibacterial peptide of the present invention for use in the treatment of sepsis. Yet a further aspect concerns the use of a vector (such as a recombinant phage) encoding and adapted for expression an antibacterial peptide of the present invention for the preparation of a medicament for the treatment of sepsis.

It follows that the medicaments described herein may be in a form to be administered through an oral, intravenous, an inhalation, intramuscular or subcutaneous route. In another embodiment, the medicaments is in a form to be administered topically, such as for the treatment of an infected wound.

Bacteria

The bacteria may be any bacteria, which are susceptible modulation of the dinQ expression, or in which dinQ expression induce cytotoxicity.

The bacterium is preferably a gram negative, even more preferably the bacterium is selected from the group of pathogenic *E. coli, Salmonella, Campylobacter, Shigella, Klebsiella, Staphylococcus aureus, Bacillus subtitles, Bacillus cereus* and *Neisseria meningitidis*.

In one embodiment, the antibacterial DinQ polypeptides, polynucleotides and expression vectors encoding the same for use for reducing the load of or inhibition of propagation of a bacterium resistant to commonly used antibiotics such as in the treatment of multidrug resistant bacteria.

Delivery

Delivery of polynucleotide, heterologous genes, or polypeptides of the invention may be done by direct injection, by the use of carrier lipids, by the use of carrier peptides, or using a phage derived vector system.

Since the DinQ polypeptides causes membrane depolarisation and ATP depletion of the bacteria (Example 7 and 8), the method of the invention can be used to increase the sensitivity of a bacterium to other antibiotics.

Thus, in one embodiment of the invention, the antibacterial DinQ polypeptides or polynucleotides encoding the same are used in combination with another antibiotic such as an antibiotic is selected from the group consisting of: rifamycine, aminoglycosides, carbapenems, cephalosporins, cephems, glycopeptides, fluoroquinolones/quinolones, macrolides, oxazolidinones, penicillins, streptogramins, sulfonamides, and tetracyclines. Most preferably, the antibiotic is rifamycin or quinolone.

In yet a further embodiment, said at least one other antibiotic is selected from nucleic acid synthesis inhibitors such as nalidixic acid and mitomycin C, protein synthesis inhibitors such as tetracycline, cell wall inhibitors such as ampicillin, and metabolic inhibitors such as erythromycin.

General

Reference to any prior art in this specification is not, and should not be taken as, an acknowledgment or any form of suggestion that this prior art forms part of the common general knowledge in any country.

All patent and non-patent references cited in the present application, are hereby incorporated by reference in their entirety.

As will be apparent, preferred features and characteristics of one aspect of the invention may be applicable to other aspects of the invention. The invention may be embodied in other specific forms without departing from the spirit or essential characteristics thereof. The foregoing embodiments are therefore to be considered in all respects illustrative rather than limiting on the invention described herein. Scope of the invention is thus indicated to be the appended claims rather than by the foregoing description, and all changes that come within the meaning and range of equivalency of the claims are intended to be embraced by reference therein.

It should be understood that any feature and/or aspect discussed above in connection with the methods according to the invention apply by analogy to the prevention of antibiotic resistance or prevention of the development of antibiotic resistance.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention will hereinafter be described by way of the following non-limiting Figures and Examples.

FIGURE LEGENDS

FIG. 1
Overview of the dinQ/agrAB Locus

A. Genomic organization of agr-dinQ locus in E. coli. This locus contains three genes originating from separate promoters; two constitutively expressed transcripts, agrA and agrB (grey box), and one divergently transcribed gene, dinQ (grey box), which is regulated by the LexA binding site during the SOS response. Transcription initiation sites are indicated by color-coded arrows.

B. Sequence of the full length ars gor intergenic region with hallmarks (SEQ ID NO: 23). Promoter elements, −10 and -35, LexA boxes and terminator sequences are underlined. Transcription start ( ) and stop ( ) for dinQ, agrA and agrB has been experimentally determined. The ars gor intergenic sequence contain repeat sequences, agrAB repeat (shadowed). The agrAB repeat of dinQ is antisense to sequences in the agrA and agrB transcripts and the alignment of these is shown in D.

C. Sequence of the fullength dinQ transcript with annotated open reading frames (SEQ ID NO: 24). The dinQ transcript contains two open reading frames encoding putative peptides of 18 and 49 aa, in which the 49 aa ORF contain four putative start codons (underlined and assigned), ORFii of 49 aa, ORFiii of 42 aa, ORFiv of 38 aa and alternative transcription start codon GTG at ORFv of 27 aa. Notably, ORFv is the only translated reading frame in vivo, see text. Terminator sequences are underlined.

D. Alignment of agrAB (SEQ ID NOs: 25 and 26) sequence antisense to dinQ (SEQ ID NO: 27).

FIG. 2
dinQ Expression Pattern and Transcription Start

A. Northern analysis of dinQ and agrAB transcripts. A riboprobe specific to either dinQ or agrAB was hybridized to a Northern blot with total RNA extracted from strains lacking dinQ, agrA or agrB compared to wt AB1157 before and after UV exposure. Transcription pattern as indicated with alternative transcripts dinQ-a-b-c-d suggests a complicated regulation of transcription initiation according to the antisense homologue sequence to agrA and agrB. dinQ-b is up-regulated in agrB confirming that agrB is a regulator of dinQ gene expression.

B. A [$^{32}$P] labelled primer specific to dinQ was used to investigate the point of transcription initiation of the alternative dinQ transcripts according to the expression pattern shown in A (see materials and methods for details). The primer was hybridized to total RNA extracted from strains lacking RNaseIII (SK7621), agrA (BK4042) or agrB (BK4043) and compared to wt AB1157. Signals detected was correlated in size and intensity to the Northern blot in A and assigned according to that (SEQ ID NO: 28). dinQ-b is of main interest because of the phenotype observed with the agrB mutant.

C. A [$^{32}$P] labeled primer specific to agrAB was used to investigate the point of transcription initiation of agrAB. Total RNA from a strain lacking agrB (BK4043) was used to localize agrA transcription start (SEQ ID NO: 29) and vice versa for agrB (BK4042) localization (SEQ ID NO: 30) due to the transcripts sequence homology (see materials and methods for details). The point for transcription initiation is indicated with an asterix (red) for each transcript.

Figure 3:
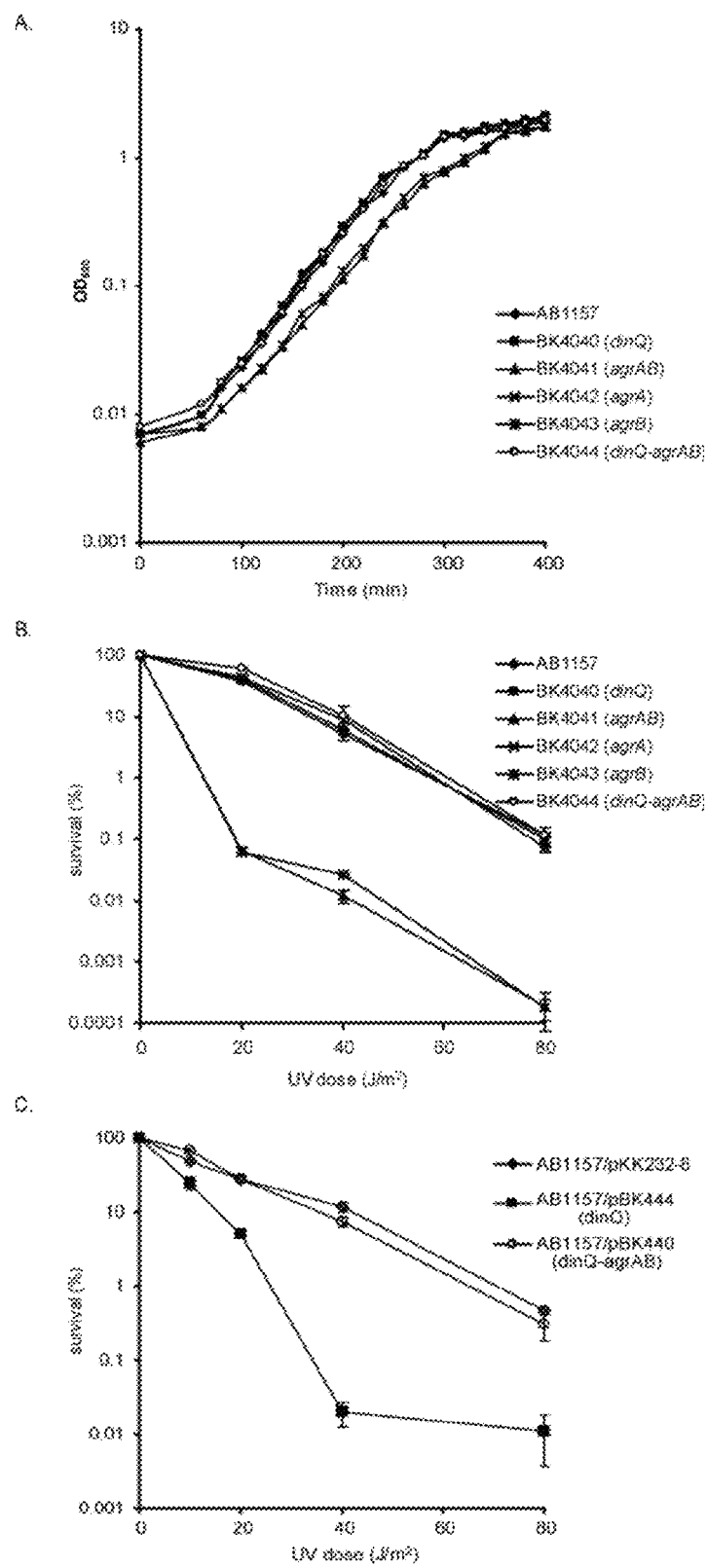

FIG. 3
Mutant Phenotypes

A. Growth rates of wild type compared to dinQ (BK4040) and agrAB single and double mutant combinations (agrAB BK4041/agrA BK4042/agrB BK4043/dinQ-agrAB BK4044). The agrB single and agrAB double mutant displayed a prolonged lag phase compared to the other strains investigated.

B. UV-survival of dinQ, agrA and agrB single mutants, agrAB double mutant and the agrAB dinQ triple mutant. The agrAB double mutant and agrB single mutant is extremely sensitive to UV irradiation. Deletion of dinQ in the agrAB mutant making a triple mutant relieves the UV sensitivity of the double mutant, indicating that the agrB transcript is important for antisense control of dinQ transcription.

C. UV survival of wild-type E. coli over expressing dinQ-agrAB (pBK440) or dinQ (pBK444). High expression levels of dinQ makes the cell sensitive to UV irradiation in a similar manner as deletion of agrB. Co-expression of agrAB together with dinQ relieves the UV sensitivity of dinQ alone indicating that the agrB transcript plays an important role regarding regulation of dinQ transcription.

Figure 4:
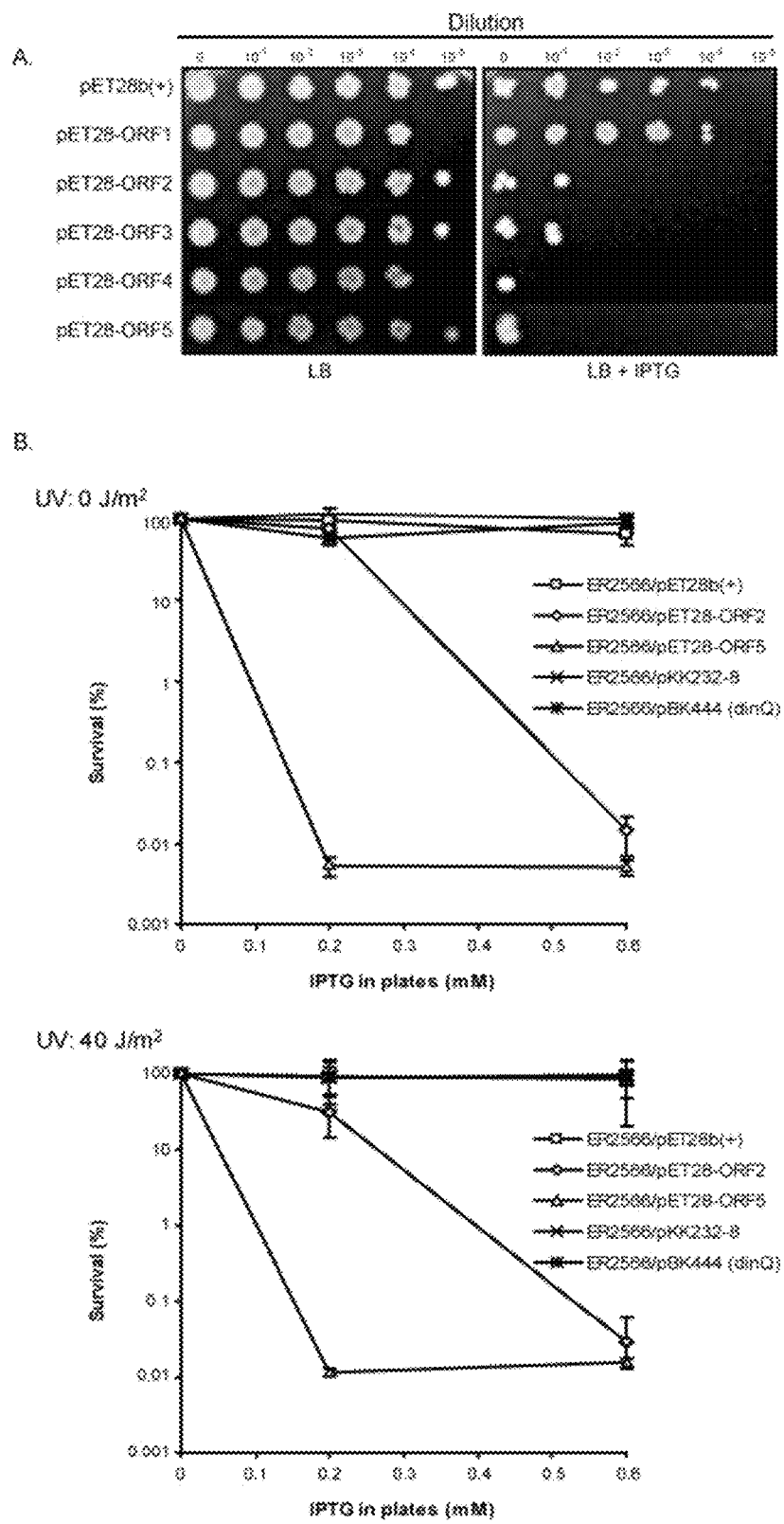

FIG. 4
Toxic Phenotypes

A. IPTG sensitivity in strains plated on IPTG. An aliquot or serially diluted (10-1-10-5 cells ml-1) log-phase cultures of wild type E. coli with empty expression vector pET28b(+) or vector constructs with alternative DinQ ORFs were spotted onto LB plates containing no IPTG (left panel) or 0.6 mM IPTG (right panel). The growth indicates a toxic effect with DinQ ORF 2-5 when the translation is forced by IPTG induction.

B. IPTG-survival of wild-type E. coli over-expressing putative dinQ encoded peptides related to UV exposure. Upper panel show the effect of IPTG induction without UV exposure, lower panel show the effect of IPTG induction after UV exposure. The toxic effect observed is caused by IPTG induction and thereby overproduction of the peptide, not induction of the SOS response by UV irradiation.

Figure 5:
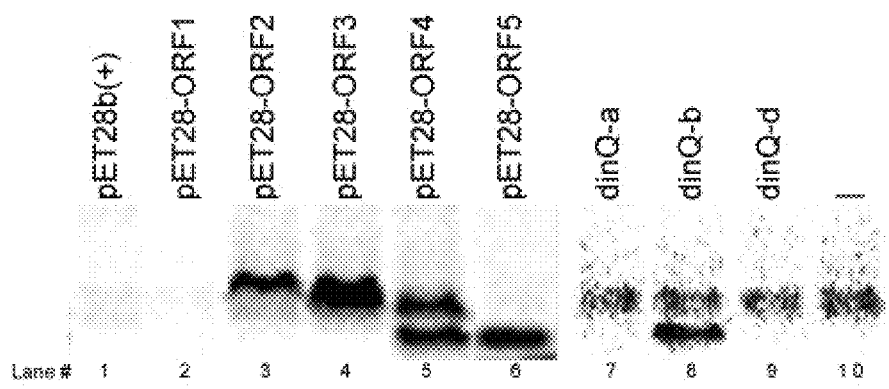

FIG. 5
In vitro transcription/translation assay with [14C]-Leucine with the different DinQ open reading frame constructs (ORF1-2-3-4-5) and dinQ DNA templates (dinQ-a-b-d) were carried out as described in materials and methods. There are peptides translated from all ORFs except ORF1 with decreasing size. A peptide of similar size as ORF5 is translated from alternative dinQ transcript dinQ-b indicating ORF5 as the active translated DinQ peptide.

Figure 6:
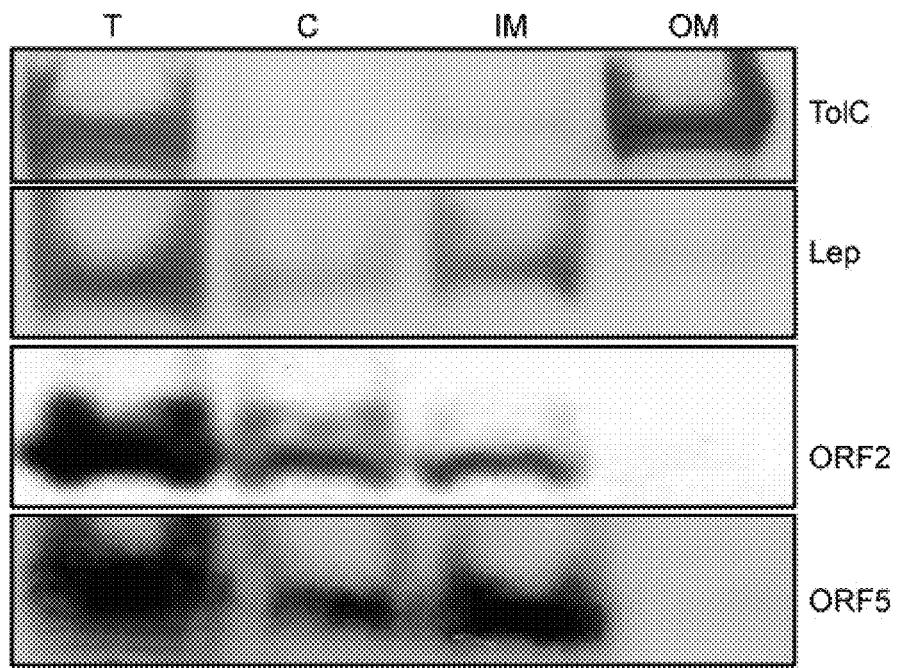

FIG. 6
Localization of Flag-Tagged DinQ.

Cells were harvested after IPTG induction and total protein extracts were fractionated as described in materials and methods. Fractions was analysed by Western blotting using antibodies against FLAG, Lep and TolC. Lep and TolC were used as established IM and OM marker proteins respectively. T: total protein; C: cytoplasmic fraction; IM: inner membrane fraction; OM: outer membrane fraction.

FIG. 7

DinQ Peptide Structure

A. The DinQ ORF V peptide consist of 20 hydrophobic amino acids and 7 hydrophilic amino acids.

B. Computational model of DinQ ORF V indicate a single transmembrane domain. The model shows four successive 90 degree rotations of the transmembrane peptide.

FIG. 8

Alignment of sequences generating translational active transcripts of TisB (SEQ ID NO: 31) and dinQ (SEQ ID NO: 32). The nucleotides in bold is indicating cleavage site. Putative recognition sequence for cleavage enzyme is underlined.

FIG. 9

Membrane Depolarization Upon DinQ Overproduction

Changes in membrane depolarization upon DinQ ORF2 and -ORF5 overproduction examined by flow cytometry as described in materials and methods.

A. Control cells with empty vector pET28b(+) at 0, 5 and 20 minutes after addition of IPTG, staining with DiBAC4(3) and 10.000 cells were counted.

B. Cells over-expressing DinQ ORF2 0, 5 and 20 minutes after addition of IPTG, staining with DiBAC4(3) and 10.000 cells were examined by flow cytometry.

C. Cells over-expressing DinQ ORF5 at 0, 5 and 20 minutes after induction with IPTG was stained with DiBAC4(3) before 10.000 cells were counted and examined by flow cytometry.

The graphs are representative of at least three repetitions.

FIG. 10

Intracellular ATP Concentration

The staple diagram shows ATP concentrations before and 20 minutes after addition of IPTG to control cells AB1157 and mutant agrB (BK4043) cells. ATP concentrations were determined by a luciferase-based assay (Promega) see materials and methods for details.

FIG. 11

DNA content histograms of control strain AB1157 (upper panel row) and agrB mutant (BK4043) (lower panel row) grown in ABTGcasa at 37° C. with indicated time points after with rifampicin treatment. Distinct peaks represent the accumulation of cells with integral numbers of chromosomes that reflect the numbers of origins at the time of drug action.

FIG. 12

RT-qPCR

The staple diagram shows quantitatively amounts of the SOS response regulator genes recA and lexA related to dinQ and agrAB mutants. There are no significant differences in recA and lexA expression level between the control strain AB1157 and the mutants concluding that the genes investigated shows no effect according to regulation of the SOS response in E. coli.

FIG. 13

Filamentation

Fluorescence microscopy of UV exposed (50 J/m2) cells followed by growth for 1 and 2.5 h. Cells were grown in K-medium and stained with acridine orange.

FIG. 14

IPTG Induction of ORF2 dinQ

E. coli K12 ER2738 cell densities before, following, with and without IPTG induction (1 mM) of ORF2 (dinQ) at 180 min/$OD_{600}$=0.4.

FIG. 15

E. coli K12 ER2738 survival upon exposure to phagemids containing various constructs: a control, ORF2 & ORF5 from dinQ

FIG. 16

Bacterial strains with increased levels of dinQ (BK4043) showing increased sensitivity to various classes of antibiotic. See Example 14 for further details.

FIG. 17

A map over the plasmid pORF5 which is packed into the phagemid particles and ultimately is responsible for the expression of ORF5 inside of E. coli. The map includes the following features: Bla b-lactamase, selection to stably maintain the plasmid within the propagating bacteria, F1 on the bacteriophage origin of replication to direct a ssDNA copy into the phagemid particles, pUC origin for bacterial replication and ORF5 from dinQ for expression of the toxin in the absence of lacI.

FIG. 18

Mus musculus in vivo experiments showing a 100 fold reduction in viable E. coli counts following treatment of a sepsis model. See Example 16 for further details.

FIG. 19

Peptide Secondary Structure Prediction and 3D Modeling

A. DinQ amino acid sequence (SEQ ID NO: 33) with predicted secondary structure elements (H=helix, '-'=other) and corresponding reliability index (range 0-9). B. 3D modeling of DinQ as a regular alpha-helix embedded in a lipid membrane. Polar patch formed by residues Glu17 and Arg20 encircled by dashed ellipse.

FIG. 20

Microscopy of E. coli overexpressing dinQ ORF5 upon IPTG induction. Four hours after IPTG addition many "ghost" cells are seen (2) compared to healthy E. coli (1). The data demonstrate that the dinQ ORF5 peptide damages membrane integrity in such a way that allows the passive diffusion out of the contents of the bacterium affected (see Example 18 for further details).

FIG. 21

Overexpressing dinQ ORF5 in E. coli (upon IPTG induction) leads to the appearance of small colony variants (SCV). The SCV count decreased simultaneously with the number of viable bacteria. It has been previously demonstrated that SCV are due to impaired respiration and therefore ATP production. The SCV phenotype has been shown in other bacterial species to be a result of the inhibition of respiration. A damaged inner membrane that results in reduced ATP production and subsequently limits growth could result in the phenotype seen above.

FIG. 22

UV radiation survival measurements showing the difference between wild type dinQ toxicity and dinQ when the amino acid substitutions G10K or L23I or I7V are used (see Example 20 for further details).

FIG. 23

UV radiation survival measurements showing the difference in dinQ toxicity, when dinQ contains the amino acid substitutions L12I and I13V, and the construct is subjected to UV radiation at 24 J/m$^2$ (see Example 21 for further details).

EXAMPLES

Materials and Methods/Experimental Procedures
Strains Plasmids and Media

The experiments were carried out in strains AB1157 (arg, his, leu, pro, thr, ara, gal, lac, mtl, xyl, thi, tsx, rpsL, supE and kdgK) (17), Mutants were made in strain BW25113- pKD46 (21) and introduced into AB1157 via T4GT7 transduction. Vector pKK232-8 contains a promoter less cat gene allowing for selection of DNA fragments containing promoter activity.

pBK440 (dinQ-agrAB)/pBK444 (dinQ) is based on the vector pKK232-8 (Phamacia) with a 700 bp insert from the intergenic region between ars-gor in MCS. I.e. a plasmid that expresses E. coli dinQ transcript from its own SOS inducible promoter.

Expression plasmids pET28b-ORF1, pET28b-ORF2, pET28b-ORF3, pET28b-ORF4 and pET28b-ORF5 contains the DinQ ORF1, ORF2, ORF3, ORF4 and ORFS open reading frames inserted in the NcoI-BamHI restriction sites of the pET28b(+) vector (Novagen).

Cells were grown in LB media or K-medium and washed in M9 buffer.

3×FLAG constructs obtained from GenScript co.

Example 1

Sequence Analysis

The inventors performed a search for promoter and transcriptional terminator sequences in the arsR-gor intergenic region and also a computational search of the whole E. coli genome for the 20 nt LexA binding sequence. As expected this search identified the dinQ LexA box found earlier (Fernandez de Henestrosa et al., Mol Microbiol 2000), however, a second LexA box (HI=13.82) in close proximity to the first dinQ LexA box was identified (FIGS. 1A and 1B). The search for promoters and terminators identified putative −10 and −35 sequences corresponding to the dinQ promoter which overlaps LexA box 1 and LexA box 2, and a putative dinQ terminator sequence a few nucleotides downstream of the translational stop codon of the gor gene (FIG. 1B). In addition the search for promoter and terminator sequences identified two new genes, termed agrA and agrB, containing consensus like −10 and −35 sequences and rho independent terminator sequences (FIGS. 1A and B). AgrA and agrB are transcribed in the opposite direction of dinQ.

Example 2

Northern Blot

RNA was isolated as previously described (Saetrom, P., Sneve, R., Kristiansen, K. I., Snove, O., Jr., Grunfeld, T., Rognes, T. and Seeberg, E. (2005) Predicting non-coding RNA genes in *Escherichia coli* with boosted genetic programming. Nucleic Acids Res., 33, 3263-3270). RNA samples (5 µg) were denatured at 95° C. in gel loading buffer (95% formamide, 0.025% SDS, 0.025%, Bromophenol Blue, 0.025% Xylene Cyanol, 18 mM EDTA, (Ambion)) separated on a denaturing 8% polyacrylamide gel with lxtaurin and transferred to nylon membrane (Hybond XL, Amersham) by electroblotting.

Radiolabeled RNA probes were synthesized with MAXlscript (Ambion) and hybridized using ExpressHyb Hybridization Solution (BD biosciences). Hybridization signals were visualized on Typhoon 9410 (Amersham).

Characterization of the dinQ, agrA and agrB Transcripts

To estimate the approximate size of the dinQ, agrA and agrB transcripts, Northern blots with total RNA isolated from E. coli AB1157, BK4040, BK4042, and BK4043 were hybridized with radiolabelled riboprobes against the respective genes before and after UV irradiation (FIG. 2A). The dinQ probe generate four (a-d) signals in which the main transcript (a) migrates according to the expected size of full-length dinQ, 330 nt. DinQ c, b and d migrates as transcripts of about 290, 250 and 200 nt according to the size marker. All signals are absent in the dinQ mutant demonstrating that all four transcripts are derived from dinQ. The dinQ transcript(s) are induced in response to UV in wild type and agrA mutant but not in agrB. However, the full-length dinQ product is several fold upregulated in the agrA and agrB mutants under normal growth. These data indicate a regulatory mechanism by RNA interference. Notably, the dinQ-b signal is much stronger in the agrB mutant as compared to the wild type and agrA mutant while the dinQ-c product is much weaker in the agrB mutant. These results indicate that agrA and agrB interfere differently with the dinQ transcript.

Example 3

Primer Extension

The RNA sample, 10 mg/40, was combined with 10 µl (100 000 CPM) of g-32P-ATP labeled primer and 1 ml 5× hybridization buffer (250 mM HEPES-KOH pH 7.5, 500 mM KCl). The hybridization mixture was heated to 75° C. in a cover heated thermo cycler and cooled down to 25° C. over a period of 90 minutes. The extension reaction was performed by combining the hybridization mixture with 2.5 ml of 5× elongation buffer (125 mM Tris-HCl pH 8.5, 125 mM HCl, 25 mM DTT, 25 mM MgCl2) and 5 ml dNTP-mix (1 mM dNTP, 40U AMV Reverse Transcriptase (Promega), tot 50 µl) and incubated for 30 minutes at 42° C. The extension product together with sequencing reactions (Thermo Sequenase Radionlabeled Terminator Cycle Sequencing Kit, usb) primed with the same primer was separated on a sequencing gel. Primer extension signals were visualized on Typhoon 9410 (Amersham).

Primer extension of dinQ RNA revealed transcript starts at 0, +44 and +125 corresponding to the estimated size of dinQ-a, -b and -d, respectively (FIG. 2B). In agreement with the Northern analysis the inventors find that the +44 primer extension product is much stronger in the agrB mutant as compared to wild type and agrA while the +125 product is weaker.

The agrA/B probes showed that the agrB transcript migrates slightly slower than the agrB transcript, and none of the transcripts were regulated in response to UV irradiation (FIG. 2A). Transcript start of the homologous agrA and agrB genes was mapped to the same position by primer extension (FIG. 2B), indicating that the transcripts are processed/terminated differently at the 3' end.

Example 4

In Vitro Transcription/Translation

In vitro transcription/translation on circular pET28b(+) templates or linear PCR products was performed in line with Promegas protocols *E. coli* T7 S30 Extract System for Circular DNA and *E. coli* S30 Extract System for Linear Templates respectively with [$^{14}$C] Leucine as radiolabeled amino acid. The translation products were analysed by SDS-PAGE and visualized on Typhoon 9410 (Amersham).

Example 5

Protein Fractionation/Membrane Localization

Aliquots of bacterial culture were taken 20 minutes after IPTG induction (1 mM) and harvested by centrifugation.

Pellets were resuspended in 4 ml of 50 mM phosphate buffer pH 7.2 and sonicated three times for 15 seconds. Further fractionation was performed as described by Unoson and Wagnar (2008). Proteins from all fractions was acetone-precipitated 1:1 overnight at −20° C., pellet after centrifugation was resuspended in 4×NuPAGE sample loading buffer (Invitrogen) and loaded onto 10% NuPAGE Novex Bis-Tris gels (Invitrogen).

Example 6

Immunoblotting

Protein fractions run on 10% NuPAGE Novex Bis-Tris gels (Invitrogen) were transferred to a PVDF membrane by electroblotting. Membranes were further blocked in PBS/3% BSA for 1 hour and incubated at least 1 hour with primary antibody anti-FLAG M2-alkaline phosphatase (SIGMA) (1:1.000 in PBS/3% BSA), anti-TolC (kindly provided by prof Koronakis) (1:2.000 in PBS/3% BSA) or anti-Lep (kindly provided by Prof de-Gier) (1:10.000 in PBS/3% BSA). The membranes were washed thrice in PBS/0.05% Tween prior to incubation with secondary antibody (Sigma) specific to the origin (1:30.000 anti-mouse/anti-rabbit) of the primary antibody for at least 1 hour. After 2 washes in PBS/0.05% Tween and one wash in 0.9% NaCl/10 mM Tris pH 7.5, ECL solution (Amersham Biosciences) was added to develop the blot. Western blot signals were visualized on Typhoon 9410 (Amersham Biosciences).

Subcellular fractionation and western blot experiments were performed to determine intracellular localization of DinQ ORF2 and -ORF5. As antibodies against the native DinQ ORF2 and -ORF5 could not be obtained, the inventors introduced a 3×FLAG epitope upstream of the dinQ ORF2 and -ORF5 coding gene in the pET28 based construct. Spot assays verified that both FLAG-ORF2 and -ORF5 was active (data not shown). Cells were harvested at several time-points after induction of expression to test the level of expression. FLAG-ORF2 and -ORF5 was not detectable before IPTG induction but from 5 to 40 min the inventors observed increasing levels of both peptides (data not shown). Cells were fractionated (cytosol, inner-membrane and outer-membrane) and loaded on a denaturing SDS-PAG as described in materials and methods. Antibodies against Lep and TolC were used as positive controls for inner and outer membrane fractions, respectively. The cytoplasmic fraction is partly contaminated with inner membrane; however, the outer and inner membrane fractions are clean preparations without cross-contaminations. FIG. 6 shows that both FLAG-ORF2 and -ORF5 is distributed in a similar manner as the inner membrane marker Lep and confine DinQ ORF2 and -ORF5 to be localized to the inner membrane of E. coli.

Example 7

Flow Cytometry

Cells were grown to OD600≅0.4 in LB and then induced with IPTG to a final concentration of 1 mM. At 0, 5 and 20 minutes culture samples were diluted 1:10 in filtered AB minimal medium (Clark and MaalØe, 1967) +10 μg ml-1 DiBAC4(3) (Sigma-Aldrich). After 20 minutes incubation in the dark at room temperature, cells were analysed in a Flowcytometry LSRII (Becton Dickinson) equipped with an argon ion laser and a krypton laser (both Spectra Physics). DiBAC4(3) was detected in channel 580 using 488 nm laser. Parameters were collected as logarithmic signals. The two populations were easily separated in each staining experiment. The data obtained was analyzed by winMDI software.

DinQ Overexpression Depolarize Cellmembrane

Figure 9:
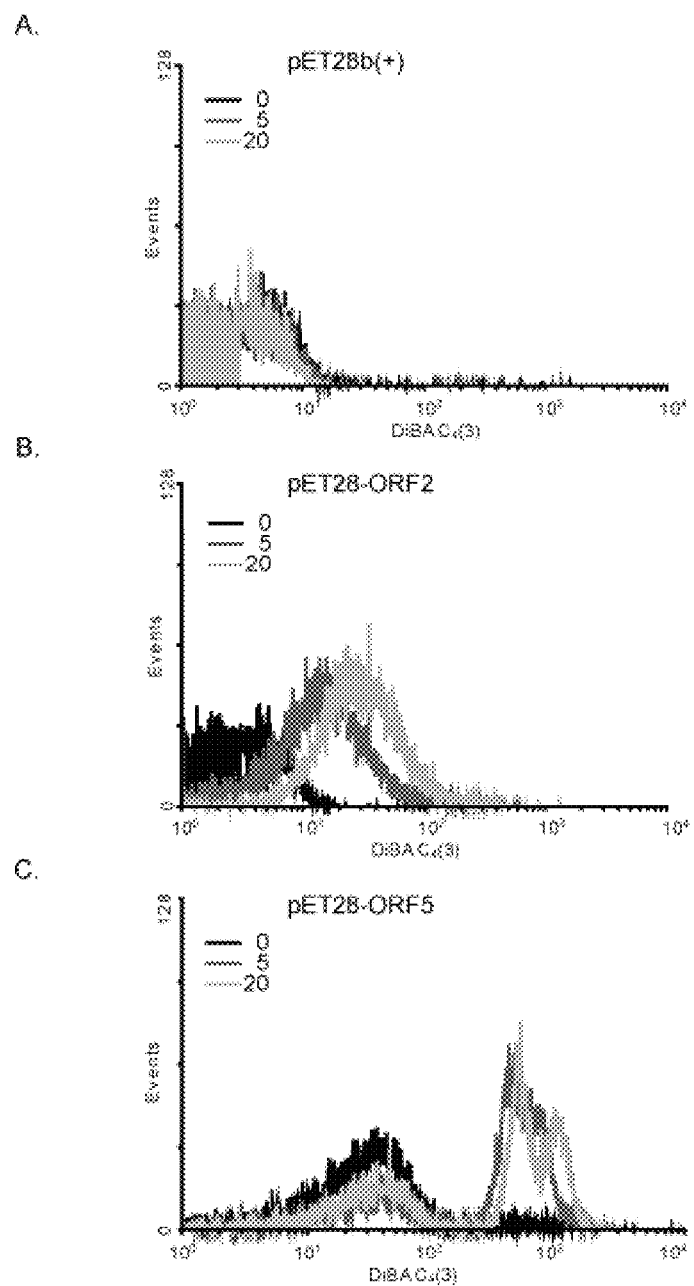

To examine whether DinQ affects membrane polarization, the inventors tested the ability of E. coli cells with dinQ containing plasmids to take up the dye DiBAC4(3) [bis-(1, 3-dibarbituric acid)-trimethine oxanol]. The dye enters cells upon membrane depolarization leading to increased fluorescence. Cells were taken 5 and 20 minutes after induction of DinQ expression with IPTG, incubated with DiBAC4(3) for 20 min and analyzed by flow cytometry (FIG. 9). No changes was observed for the plasmid control pET28b(+). Induction of DinQ-ORF2, -ORF3 (data not shown), -ORF4 (data not shown) and ORF5 showed rapid and dramatic effects on the membrane integrity suggesting depolarization of the cell membrane with induced levels of the DinQ peptide. The effect on DiBAC uptake is most pronounced for cells carrying pET28-ORF5 suggesting that DinQ ORF5 is the biologically active peptide expressed in vivo.

Example 8

ATP Assay

Aliquots of cells were harvested before and 20 minutes after induction with IPTG to a final concentration of 1 mM and washed once in 50 mM Tris-Acetate pH 7.75. ATP was extracted from washed cells by 1% (TCA) trichloraceticacid in 50 mM Tris-Acetate pH 7.75 for 10 minutes. Tris-acetate buffer (1 ml) was added 1:10 to obtain optimal pH of 7.75 before mixing with rL/L reagent (ENLITEN ATP assay, Promega) at room temperature. The amount of ATP extracted (RLU value) was measured with 20/20 Luminometer (Turner Designs) and related to the OD600 for each sample.

DinQ Overexpression Decrease Intracellular ATP Concentrations

The Western blot analysis of the cellular fractionation results in FIG. 6 showed that DinQ is localized to the inner membrane of E. coli. Therefore, the inventors suggest that DinQ might compromise the inner membrane integrity, which would be expected to affect the proton motive force, thereby affecting ATP generation and possible permit leakage of nucleotides. The effect of DinQ peptide on the intracellular ATP concentration was measured using a quantitative luciferase-based assay (see materials and methods for details). The inventors chose to measure the ATP level in the agrB mutant BK4043 in which the DinQ peptide (dinQ-b) is shown to be up-regulated and not lethal under normal physiology (FIG. 2). Extracts from uninduced and SOS-induced agrB cells and wild-type cells, AB1157, were analysed 20 minutes after exposure by UV irradiation (sublethal doses).

SOS Induction.

Figure 10:
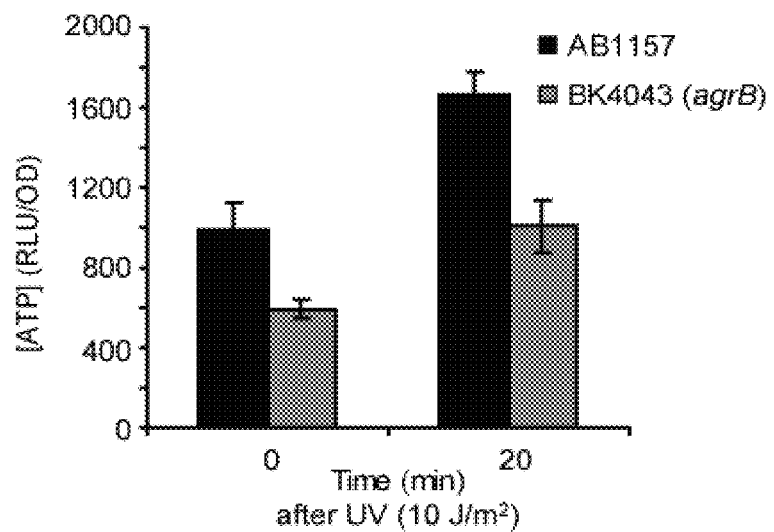
Figure 11:
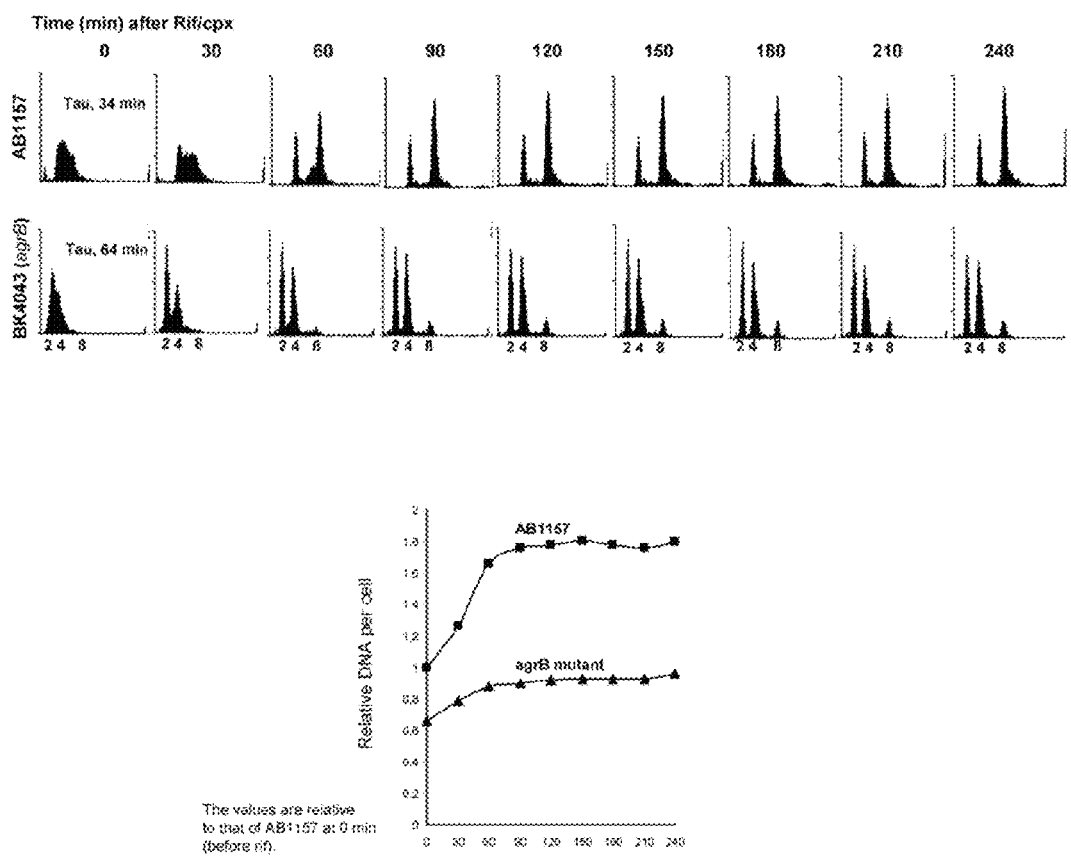
Figure 12:
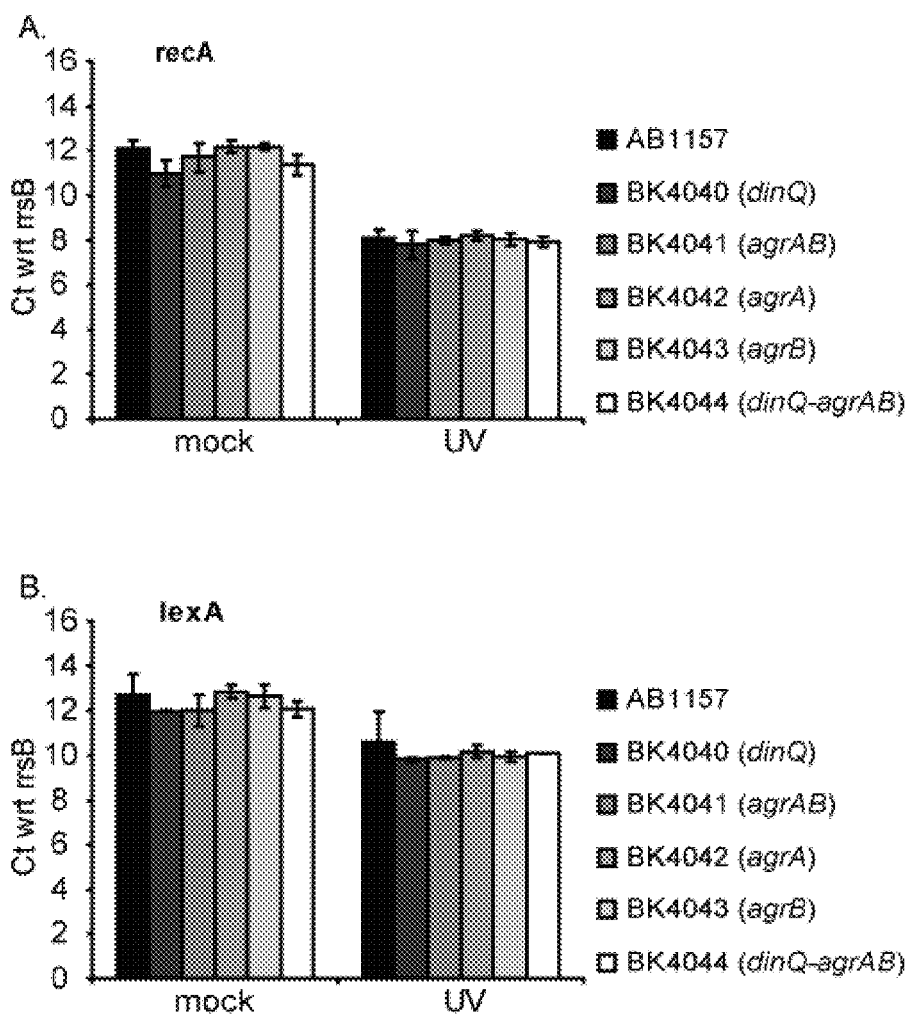
Figure 13:
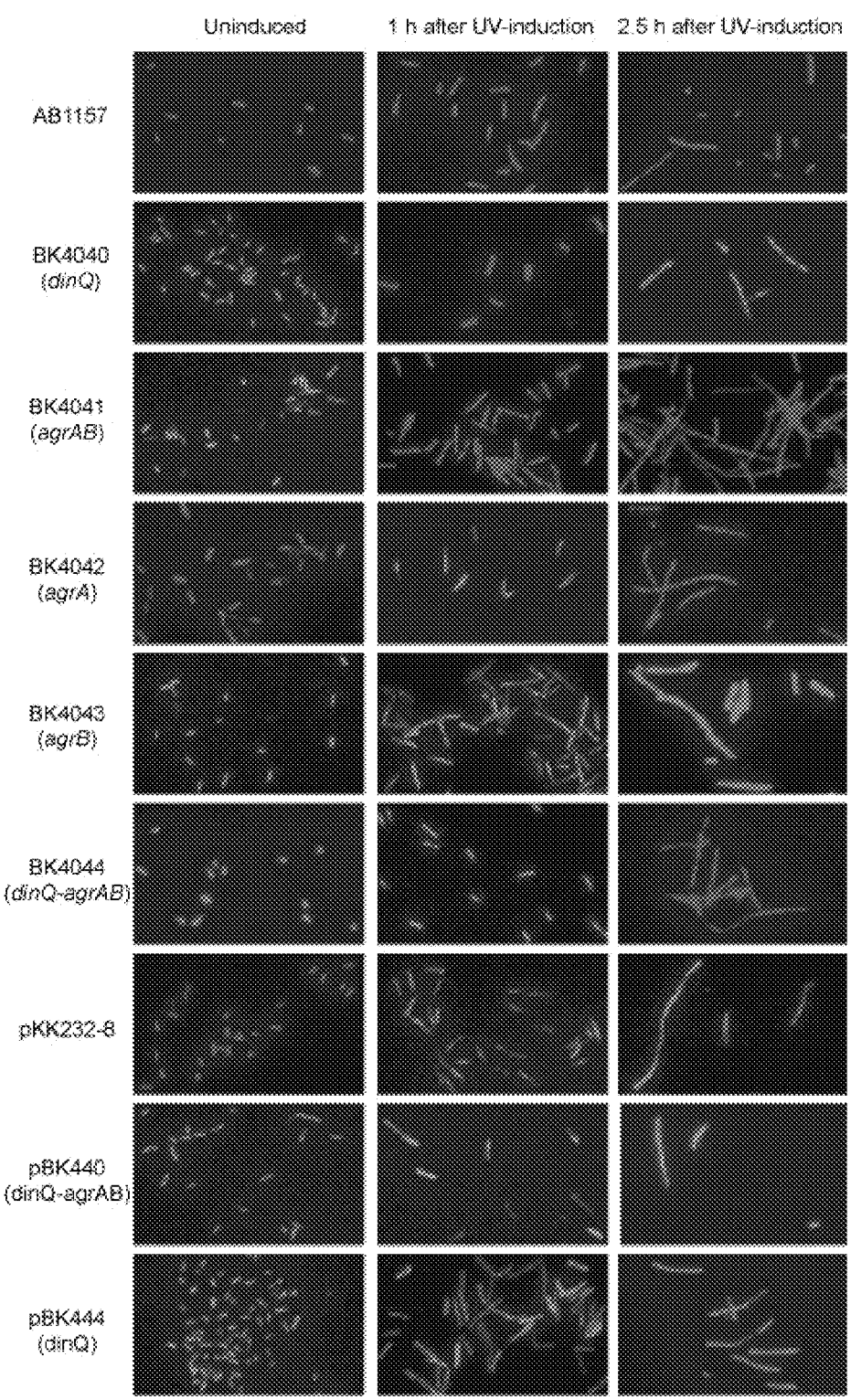

The ATP concentration in agrB cells was significantly lover compared to wild type AB1157 before UV-irradiation, FIG. 10. Twenty minutes after SOS induction the ATP concentration increased approximately 0.8 times in both strains. Thus, overproduction and insertion of the DinQ peptide into the inner membrane of E. coli impairs the energy supply in the form of ATP.

Example 9

Deleting agrB Results in UV Sensitivity

The 34 nt antisense region in agrB gene indicate a function in antisense regulation of dinQ. This antisense sequence is partially complementary in agrA suggesting that both the agrA and agrB transcripts could basepair with the dinQ transcript. To examine the role of agrA and agrB in regulating dinQ, three single mutants, one double mutant and one triple mutant were constructed. The agrA (BK4042), agrB (BK4043) and dinQ (BK4040) single mutants were generated by deleting each of the genes and introducing a kanr cassette. Next, the agrA agrB double mutant (BK4041) was generated by deleting both genes and introducing a kanr cassette. To construct a triplemutant the entire arsR-gor intergenic region containing dinQ, agrA and agrB was deleted (BK4044) and replaced with the kan$^r$ cassette. To ensure the function of dinQ, the deletions of agrA and agrB was made without destroying the dinQ operator. dinQ belong to the LexA regulon in *E. coli* which regulates the SOS response. Several mutants of the SOS response, which play a direct role in DNA repair, display UV sensitivity. To examine the role of the dinQ-agrAB locus in the SOS response the inventors tested UV sensitivity of the various mutants (FIG. 3B). The agrB single mutant and agrA-agrB double mutant showed a significant increase in UV sensitivity compared to the isogenic wild type strain AB1157. In contrast, the agrA and dinQ single mutants and the dinQ agrA agrB triplemutant showed no UV sensitivity. These data indicate a role for agrB in protection to UV exposure, in which the agrB transcript modify the dinQ transcript. According to the Northern blot (FIG. 2A) agrB repress accumulation of the +44 dinQ/dinQ-b transcript. It thus appears that the +44 dinQ product mediates the UV sensitivity of the agrB mutant.

Example 10

Over-Expression of dinQ

To further investigate the role of the gor-arsR inter genic region in UV protection, the inventors cloned agrA, agrB or dinQ separately or the entire region containing all three genes in to the cloning vector pKK232-8. Wild type AB1157 transformed with the plasmid pKK232-8-dinQ showed increased sensitivity to UV as compared to AB1157 transformed with the pKK232-8 (cloning vector), FIG. 3C. AB1157 transformed with constructs expressing agrA or agrB exhibited wild type resistance to UV (data not shown). Interestingly, wild type cells transformed with the plasmid carrying the entire gor-arsR encoding dinQ showed no UV sensitivity, demonstrating that agrA/B neutralize the UV sensitizing effect of dinQ. The agrB mutant BK4043 (FIG. 3B) and the wild type cells transformed with pKK232-8-dinQ (FIG. 3C) displayed the same sensitivity to UV. These results suggest that agrB modulate the UV sensitivity induced by the dinQ expression.

Slow Growth, Small Colonies in agrB Mutant

During construction of the agrB mutant and the agrAB double mutant it was notified that the mutants were forming small colonies when plated on LB agar. To further investigate this growth phenotype the inventors compared the growth of the agrB mutant BK4043 with the growth of its isogenic wild type AB1157 in addition to the other single- double- and triple-mutants described. OD600 was measured during growth and a sample was diluted and plated for viable counts. FIG. 3A showed that the agrB single mutant and agrAB double mutant mutant dispose a delay in entry into exponential phase. These results indicate a specific independent role for agrB in regulation of the exponential growth phase entry.

Example 11

Mapping the DinQ Open Reading Frame

The mechanism underlying the UV sensitive phenotype of DinQ in a multicopy situation or under upregulation in an agrB mutant is unknown. The dinQ gene contain two putative open reading frames in which one of the reading frames encode three putative start codons (ii-iv, see FIG. 1C). None of the ORFs shows homology to known peptides. To examine if any of the open reading frames mediate the UV sensitivity each reading frame were cloned into the expression vector pET28b(+) and expressed under control of IPTG (FIG. 4A). Unexpectedly, the inventors observed that ORF-II-IV showed a strong toxic/growth inhibitory effect in presence of IPTG induction even in absence of UV, demonstrating that the sequence of ORF IV is sufficient to possess the dinQ phenotype. Next, DinQ ORF II expression was titrated with increasing concentrations of IPTG (FIG. 4C) showing that ORF IV is highly toxic to the cells at very low doses of IPTG induction. In vitro transcription-translation experiments with pET28 ORF I to IV in *E. coli* T7/S30 extracts (Promega) showed that peptides II-IV were expressed whereas no expression could be detected from ORF I (FIG. 5A). Notably, extracts with the pET28-ORF VI construct produced two peptides of approximately 4.5 and 3.5 kDa, in which the smallest peptide is indicating an alternative start codon within ORF IV. A closer inspection of the dinQ sequence indicates a Shine Dalgarno motif within ORF IV in optimal position to initiate translation at a Val codon (termed codon v in FIG. 1C), which is encoding a putative peptide of 27 aa termed ORF V. In order to examine this reading frame the inventors cloned the sequence in to pET28(+), transformed the construct in to wild type cells and monitored survival during UV exposure and IPTG induction. Similar to ORF II-VI the inventors find that ORF V display strong toxicity under IPTG expression in absence of UV (FIG. 4). Further in vitro translation in *E. coli* T7/S30 extracts with pET28-ORFV and denaturing SDS-PAGE showed that the ORF V peptide and the smallest peptide synthesized from ORF IV are identical (FIG. 5, lane 5 and 6). These results suggest that translation of ORF V is sufficient to mediate DinQ toxicity. Next, the inventors examined expression of DinQ peptide(s) in *E. coli* S30 extracts with PCR products corresponding to dinQ transcripts a, b and d as template. Interestingly, transcript dinQ-b produced a peptide identical to the size of ORFV from pET28-ORFV whereas no translation was observed with transcript a and d. These data support that the +44 dinQ (dinQ-b) transcript, which is abundant in the UV sensitive agrB mutant, is actively translated to produce the DinQ-ORFV peptide.

dinQ Structure

Figure 7:
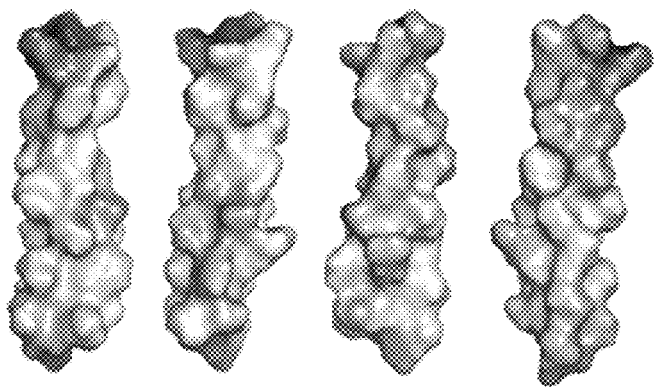

Computational modelling of the DinQ peptide ORF V indicates a single transmembrane domain (FIG. 7). Thus it appears that the DinQ peptide is spanning the inner membrane of *E. coli*. Therefore the inventors suggest that DinQ may modulate processes that occur at the inner membrane such as replication, transcription, recombination or oxidative phosphorylation.

Example 12

*E. coli* K12 ER2738 Survival Assay

Figure 14:
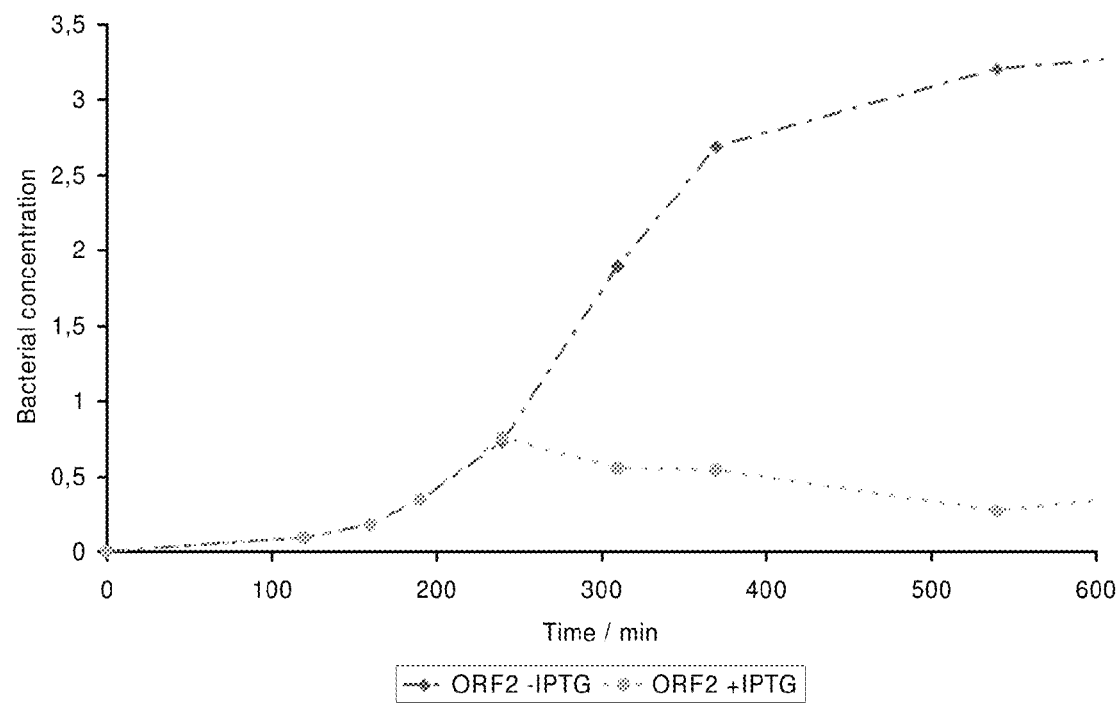

The *E. coli* K12 ER2738 cells containing a repressor plasmid and an inducible plasmid which can express ORF2 from dinQ were initially grown overnight before sub-culturing 1:100. The density of cells was then followed by measuring the optical density at 600 nm. IPTG (1 mM) was added to one of the samples once a density of 0.4 was reached. The optical density was then followed over the next 7 h. The data are presented in FIG. 14.

Example 13

E. coli K12 ER2738 Phagemid Survival Assay

Figure 15:
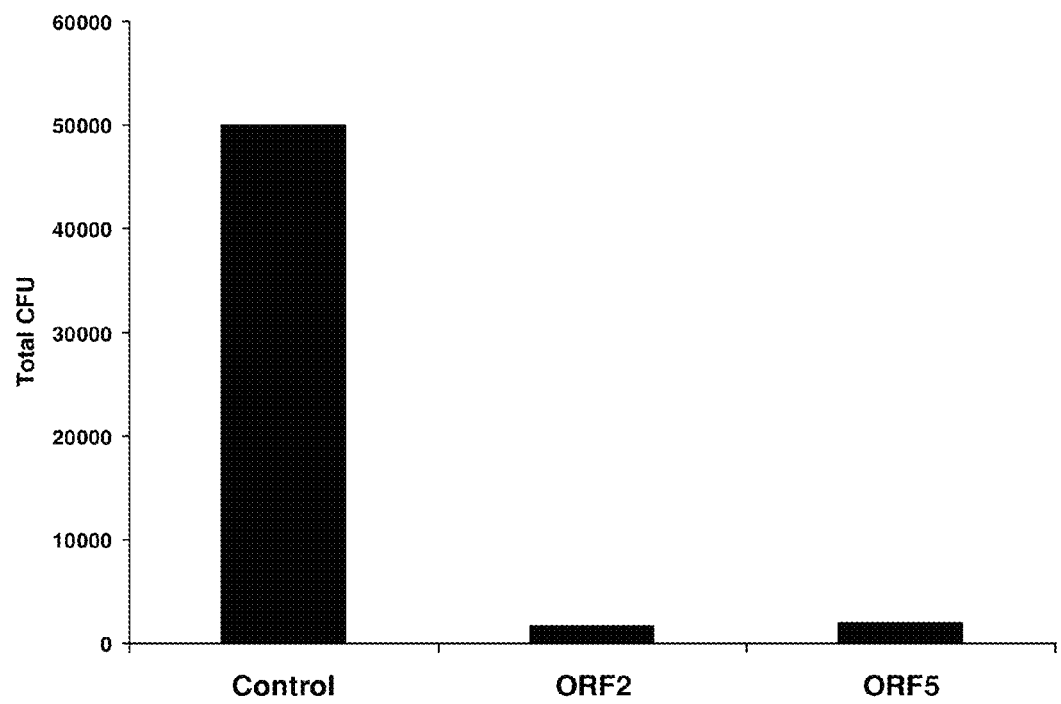

Bacteria (E. coli K12 ER2738) were grown to an OD600=0.8. The cells were then diluted to a final density of 106 CFU/ml before the addition of IPTG so that the final concentration in each suspension will be 1 mM. An aliquot of cells ($10^5$ CFU) was then mixed with an equal volume of phagemid ($8 \times 10^9$ PFU/ml) and incubated without shaking (37° C., 1 h). The solutions were plated out (LB, IPTG 1 mM) using serial dilution and the surviving colonies counted the following day. The data are presented in FIG. 15.

Example 14

Bacterial Strains with Increased Levels of Ding (BK4043) Showing Increased Sensitivity to Various Classes of Antibiotic The results for the spot assay are relative to the background strain AB1157 and a dinQ knockout strain (BK4040). Dimethyl sulfoxide (DMSO) is included as a control and a common solvent for the antibiotics studied. Ampicillin (Amp) is a broad spectrum beta-lactam antibiotic. Tetracycline (Tet) is a broad spectrum polyketide antibiotic. Mitomycin C (MMC) is an aziridine antitumour antibiotic. Nalidixic acid (Nal) is a broad spectrum quinolone antibiotic and chloramphenicol (Chl) is a broad spectrum bacteriostatic antibiotic. Log phase bacteria were diluted using a ten-fold dilution series and then plated (LB, 1.5% agar) on plates containing the antibiotic of interest at the concentrations shown. Following overnight incubation the number of surviving colonies was recorded. The data are presented in FIG. 16.

Example 15

Synthesis of the Filamentous Phagemid Particles

Figure 17:
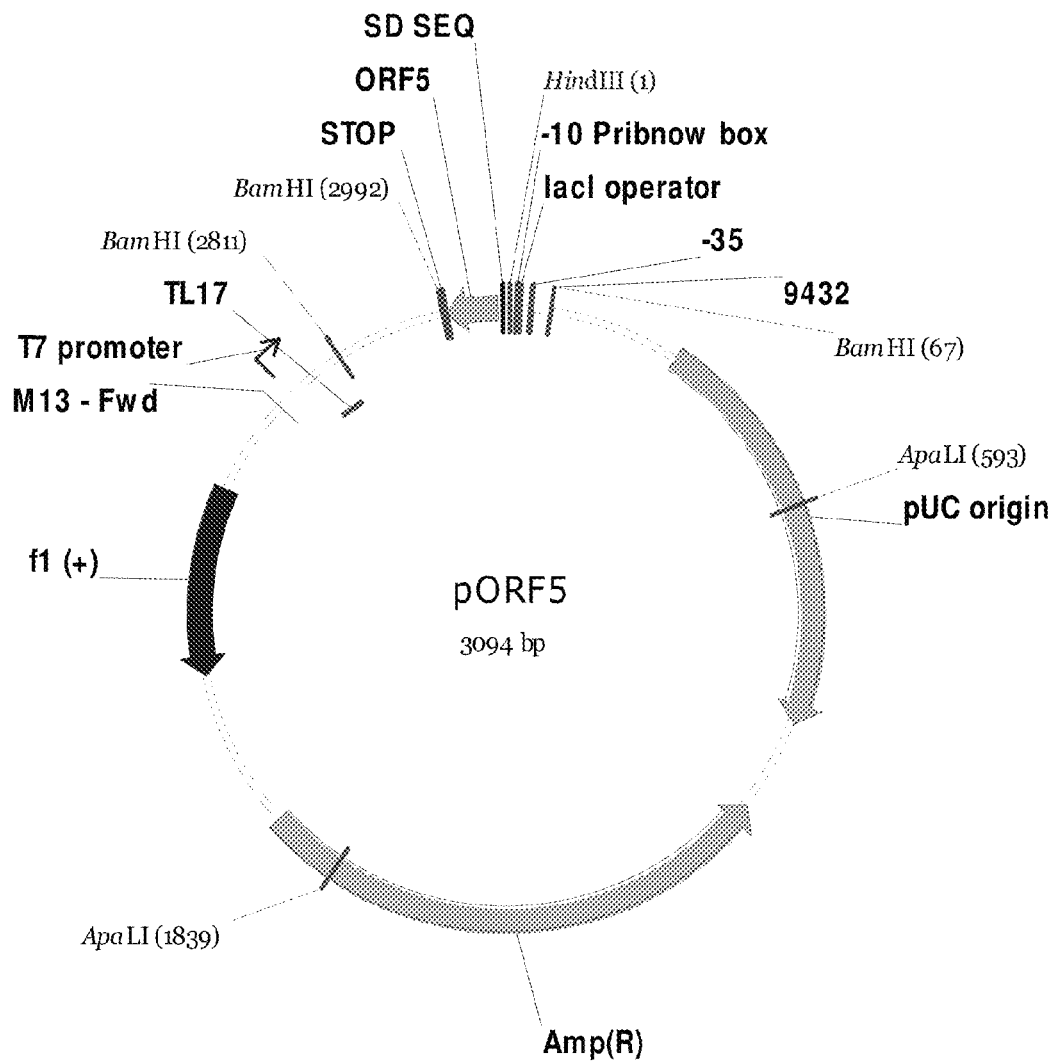

R408 helper phages were prepared and the titer calculated using standard protocols from a clearly isolated well defined plaque. An 0/N culture of ER2738 APlacITpBHR cells containing the toxic protein expression vector, e.g. pORF5 (FIG. 17 and SEQ ID NO: 18), were diluted (1:100) and allowed to grow to $OD_{600}$=0.5 at which point the cells were infected with helper phage (MOI=17). The cells were then incubated (30° C., 300 rpm, O/N) and subsequently centrifuged (3900×g, 15 min, 4° C.). The supernatants were filtered (0.2 μm) and precipitated (5% polyethylene glycol (PEG) 6000, 0.5 M NaCl, 4° C., 3 h). After collecting the phage particles by centrifugation (16,000×g, 30 min, 4° C.) they were re-suspended (5% PEG 6000, 0.5 M NaCl, 50 mM Tris-HCl (pH 7.5), 100 mM NaCl, 10 mM MgSO₄) and precipitated (4° C., 0/N). Following collection by centrifugation (16,000×g, 30 min, 4° C.) re-suspension in SM buffer (50 mM Tris-HCl (pH 7.5), 100 mM NaCl, 10 mM MgSO₄) re-centrifugation (16,000×g, 30 min, 4° C.) the supernatant was removed and the titer was calculated. A serial dilution of the phagemid solutions into a suspension of ER2738/APlacITpBHR which has been incubated (37° C., 250 rpm, 6 h) from a single colony was used for titering.

Example 16

Figure 18:
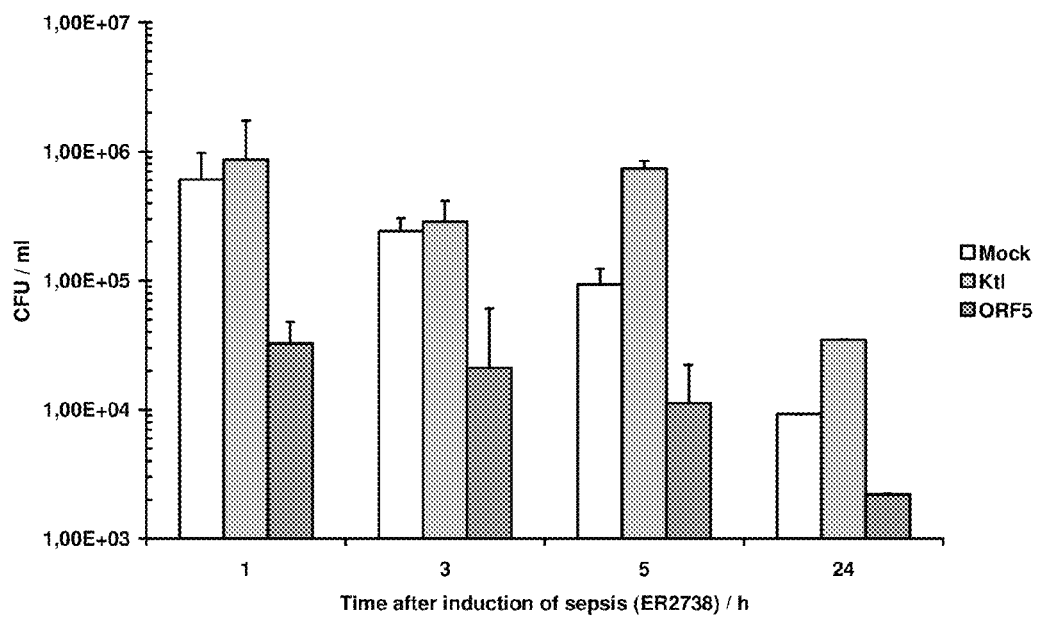

Mus musculus In Vivo Experiments Show a 100 Fold Reduction in Viable E. coli Counts Following Treatment of a Sepsis Model Neutropenia was induced by the intraperitoneal injection of cyclophosphamide (Sigma, 200 μl of a 25 mg/ml solution) six days, three days and one day before the experiment. For the experiment an O/N culture of ER2738 was diluted to $OD_{600}$=0.5 and incubated without rotation to an $OD_{600}$=1.0 (37° C.). These were injected (200 μl, ~1×10⁸ CFU) intraperitoneally together with IPTG (100 μl of a 250 mM solution) and one of the following: SM buffer (200 μl), control phagemid particles or dinQ phagemid particles (200 μl of a 1.2×10¹⁰ PFU/ml solution). Samples of blood were taken from the thigh one, three, five and 24 h after the phagemid treatment, serially diluted and plated (LB, agar 1.5%, tetracycline) to determine the bacterial load. The data are presented in FIG. 18.

Example 17

Computer Modelling of DinQ Peptide

Computer Modelling of DinQ Predict a Single Transmembrane Peptide

Figure 19:
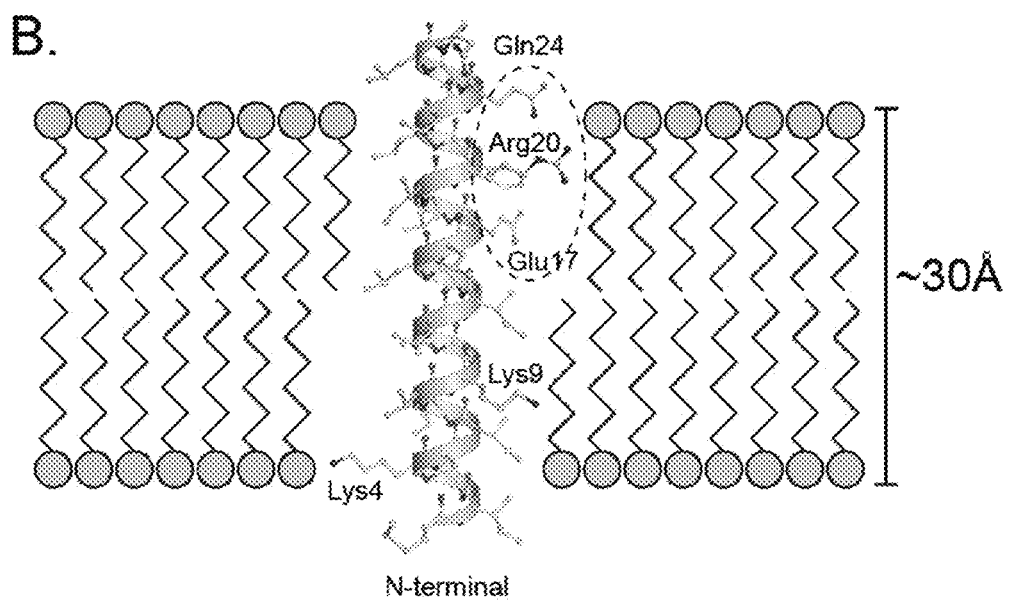

Analysis of the DinQ amino acid sequence using the consensus secondary structure prediction tool Jpred3 reveal that DinQ has high propensity to form a single alpha-helix. All residues except a few on each flanking terminal are predicted with high confidence to belong to the predicted alpha-helix (FIG. 19, A). With 20-22 residues in a single alpha-helix, the DinQ peptide could straightforwardly form a transmembrane helix of 6 full turns spanning more than 30 Å, as shown by modeling of DinQ using a regular alpha-helical template (FIG. 19, B). The two positively charged lysine residues (Lys4 and Lys9) are close to the phospholipid head groups, while particularly the charged Glu17, but also Arg20 may form a polar patch that can interact with other membrane embedded proteins (FIG. 7B).

Example 18

Abbreviations

Figure 20:
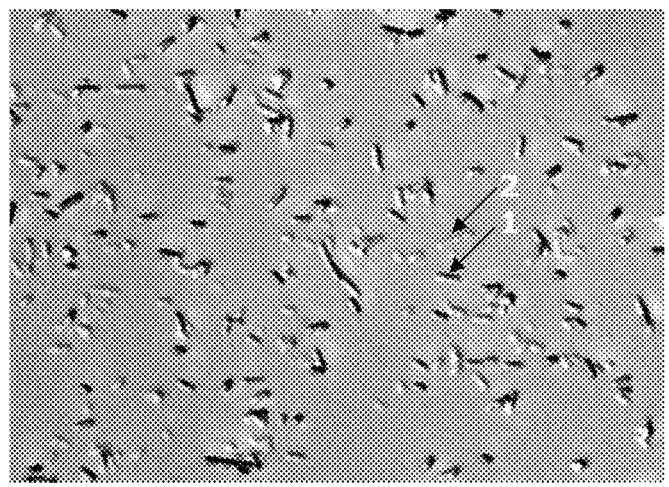

Kan Kanamycin, 100 μg/ml
Amp Ampicillin, 200 μg/ml
Tet Tetracycline, 20 μg/ml
LB Lysogeny broth
O/N Overnight
h Hours
RT Room temperature
OD600 Optical density at 600 nm
Rpm Revolutions per minute
IPTG Isopropyl β-D-1-thiogalactopyranoside E. coli capable of overexpressing dinQ ORF5 were plated (LB agar 2%, kan, tet, amp) and incubated (O/N, 37° C.). A single colony was picked and grown (37° C., 16 h, 200 rpm)

in liquid media (LB, kan, tet, amp). The culture was then adjusted to $OD_{600}=0.03$ in fresh media (LB, kan, tet, amp) and allowed to grow (37° C., 16 h, 200 rpm) back to $OD_{600}=0.5$ before induction with IPTG (1 mM). After incubation (4 h, 37° C., 200 rpm) an aliquot (200 μl) of the *E. coli* suspension was removed and fixed in MeOH (1 ml, −20° C.). After centrifugation (2000 rpm, 4° C., 5 min) the cells were aspirated and re-suspend in NaCl (0.9% in $H_2O$). The samples were then spotted onto slides and allowed to dry (42° C.). The slides were then washed $3 \times H_2O$ and allowed to air dry (RT) before microscopy (see FIG. 20).

Four hours after IPTG addition many "ghost" cells are seen. A typical *E. coli*, "1", is seen in the microscope picture×40, where the optical properties of the cell mean that it produces a heavy shadow. A typical ghost cell "2" is shown for comparison, the membrane of the organism remains intact while due to the actions of dinQ ORF5 the constituents of the bacteria can passively diffused out and be replaced by the surrounding media. This results in a cell image with much less defined shadowing. The dinQ ORF5 peptide damages membrane integrity in such a way that allows the passive diffusion out of the contents of the bacterium affected.

Example 19

Abbreviations
SCV Small Colony Variants

Figure 21:
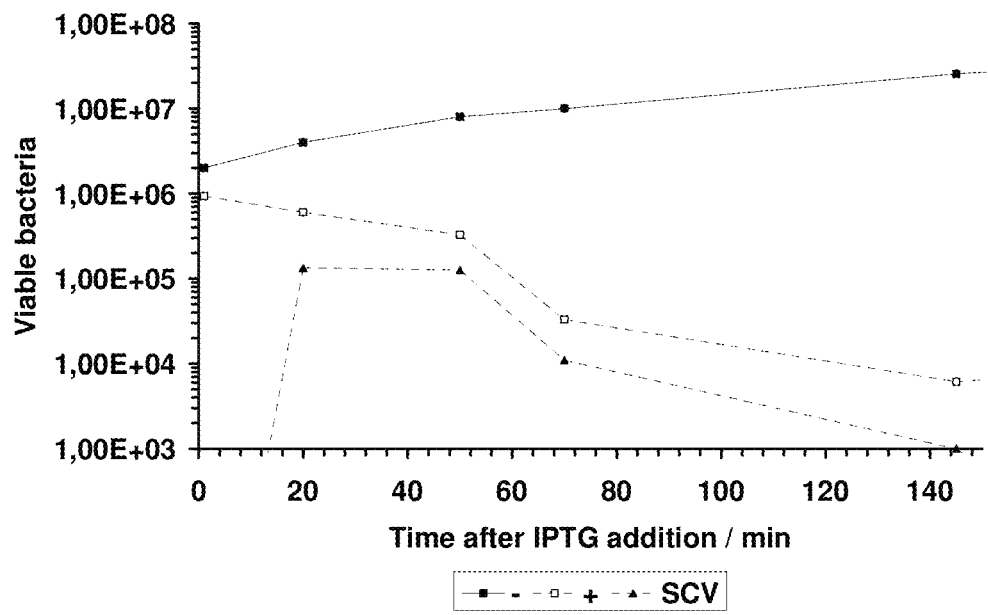

*E. coli* capable of overexpressing dinQ ORFS were incubated (O/N, 37° C., 200 rpm) before subculturing to $OD_{600}=0.01$ (LB, kan, tet, amp). After incubation (37° C., 200 rpm) to $OD_{600}=0.5$ expression of the toxin was either induced with IPTG (1 mM) or not. At time points after the addition the bacteria were serially diluted (×10) and plated (LB, 2% agar). After incubation (16 h, 37° C.) the plates were counted. Colony size was estimated and those 10× smaller than a typical colony were counted as a small colony variant SCV (see FIG. 21).

Upon induction with IPTG small colony variants, SCV, were seen, these decreased simultaneously with the number of viable bacteria between 50 and 70 minutes after treatment indicating that it was these bacteria that were being removed from the culture by IPTG treatment and therefore that the SCV could represent an intermediate phenotype during toxin killing. It has been previously demonstrated that SCV are due to impaired respiration and therefore ATP production.

Conclusion The SCV phenotype has been shown in other bacterial species to be a result of the inhibition of respiration. A damaged inner membrane that results in reduced ATP production and subsequently limits growth could result in the phenotype seen above.

Example 20

Figure 22:
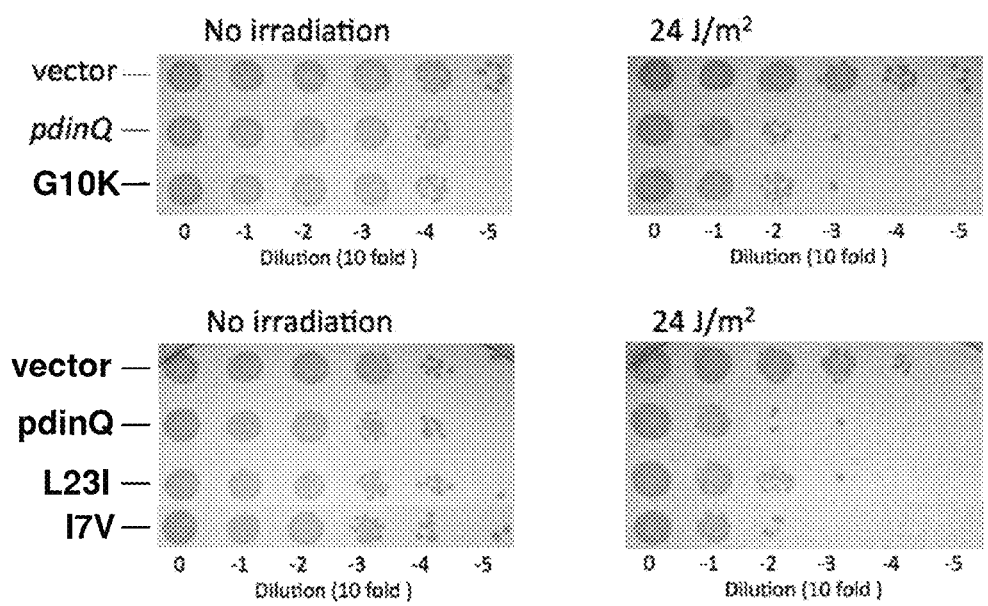

UV radiation survival measurements showing the difference between wild type dinQ toxicity and dinQ when the amino acid substitutions G10K or L23I or I7V are used (see FIG. 22). Three functional (active) single mutant variants of dinQ ORFS are provided below.

G10K
(SEQ ID NO: 19)
MIDKAIIVLKALIALLELIRFLLQLLN

L23I
(SEQ ID NO: 20)
MIDKAIIVLGALIALLELIRFLIQLLN

I7V
(SEQ ID NO: 21)
MIDKAIVVLGALIALLELIRFLLQLLN

As compared to the wild type dinQ ORF5 sequence (SEQ ID NO: 17)
MIDKAIIVLGALIALLELIRFLLQLLN The spots in FIG. 22 represent *E. coli* ER2566 dilutions in the range of 100-10-5 (left to right). UV irradiation of 24 J/m2 was used to induce dinQ toxicity (right picture), and was compared to the unirradiated control assay (left picture). Control cells carry the vector plasmid (pKK232-8), and cells carrying the plasmid encoding intact dinQ (pBK444), were used as reference. The data demonstrates that the following amino acid substitutions G10K or L23I or I7V maintain the toxicity of the dinQ peptide upon UV induction.

Example 21

Figure 23:
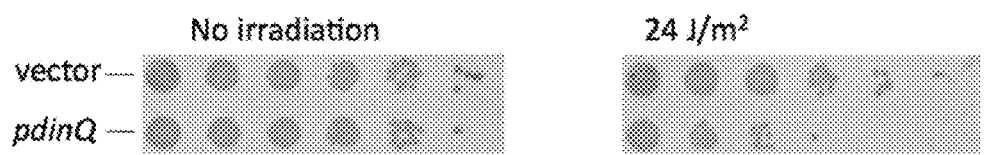

UV radiation survival measurements showing the difference between wild type dinQ toxicity and dinQ when the amino acid substitutions L12I and I13V are used (see FIG. 23). One functional (active) double mutant variants of dinQ ORF5 is provided below.

(SEQ ID NO: 22)
MIDKAIIVLGAIVALLELIRFLLQLLN

As compared to the wild type dinQ ORF5 sequence (SEQ ID NO: 17)
MIDKAIIVLGALIALLELIRFLLQLLN The spots FIG. 23 represent *E. coli* ER2566 dilutions in the range of $10^0$-$10^{-5}$ (left to right). UV irradiation of 24 J/m2 was used to induce dinQ toxicity (right picture), and was compared to the unirradiated control assay (left picture). Control cells carry the vector plasmid (pKK232-8), and cells carrying the plasmid encoding intact dinQ (pBK444), were used as reference (see FIG. 23). The data demonstrates that the following amino acid substitutions L12I and I13V maintain the toxicity of the dinQ peptide upon UV induction.

REFERENCES

Fernandez de Henestrosa et al. (2000) Molecular Microbiology 35: 1560-1572

Hemm et al. (2008) Molecular Microbiology 70(6): 1487-1501

Saetrom, P., Sneve, R., Kristiansen, K. I., Snove, O., Jr., Grunfeld, T., Rognes, T. and Seeberg, E. (2005) Predicting non-coding RNA genes in *Escherichia coli* with boosted genetic programming. Nucleic Acids Res., 33, 3263-3270

Unoson C, Wagner E G (2008) A small SOS-induced toxin is targeted against the inner membrane in *Escherichia coli*. Molecular Microbiology, 70, 258-70.

What is claimed is:

1. A method of inhibiting a bacterial infection in a subject, comprising administration of an effective amount of a pharmaceutical composition comprising a dinQ-derived polypeptide selected from the group consisting of:
   (a) a polypeptide selected from the group consisting of SEQ ID NO: 3, SEQ ID NO: 17, SEQ ID NO: 19, SEQ ID NO: 20, SEQ ID NO: 21, and SEQ ID NO: 22,
   (b) a functionally equivalent subsequence of (a) of at least 15 amino acids, and
   (c) a functionally equivalent polypeptide with a sequence identity of at least 85% to (a) or (b).

2. The method according to claim 1, wherein said pharmaceutical composition is formulated for topical, oral, pulmonary, nasal, or intraocular administration.

3. The method according to claim 1, wherein the bacterial infection is selected from the group consisting of pathogenic *E. coli*, *Salmonella*, *Campylobacter*, *Shigella*, *Klebsiella*, *Pseudomonas*, and *Streptococcus*.

4. The method according to claim 1, wherein the subject is suffering from sepsis.

5. The method of claim 1, further comprising providing to said subject at least one other antibiotic selected from the group consisting of: rifamycine, aminoglycosides, carbapenems, cephalosporins, cephems, glycopeptides, fluoroquinolones/quinolones, macrolides, oxazolidinones, penicillins, streptogramins, sulfonamides, tetracyclines, nalidixic acid, mitomycin C, ampicillin, and erythromycin.

6. The method of claim 1, wherein the polypeptide is fused to a peptide that facilitates the uptake of the fusion peptide into the target bacteria or is fused to a further polypeptide, which functions as a tag that facilitates detection and or purification of the polypeptide (purification tag).

7. The method of claim 1, wherein the polypeptide comprises natural amino acids.

8. A method of treating a bacterial infection, comprising administration of an effective amount of a pharmaceutical composition comprising a dinQ-derived polypeptide selected from the group consisting of:
   (a) a polypeptide selected from the group consisting of SEQ ID NO: 3, SEQ ID NO: 17, SEQ ID NO: 19, SEQ ID NO: 20, SEQ ID NO: 21, and SEQ ID NO: 22,
   (b) a functionally equivalent subsequence of (a) of at least 15 amino acids, and
   (c) a functionally equivalent polypeptide with a sequence identity of at least 85% to (a) or (b).

9. A method of inhibiting a bacterial infection in a subject, comprising administration of an effective amount of a pharmaceutical composition comprising a dinQ-derived polypeptide, wherein said dinQ-derived polypeptide consists of a polypeptide selected from the group consisting of:
   (a) a polypeptide selected from the group consisting of, SEQ ID NO: 7, SEQ ID NO: 9, and SEQ ID NO: 11,
   (b) a functionally equivalent subsequence of (a) of at least 15 amino acids, and
   (c) a functionally equivalent polypeptide with a sequence identity of at least 85% to (a) or (b).

10. A method of treating a bacterial infection in a subject, comprising administration of an effective amount of a pharmaceutical composition comprising a dinQ-derived polypeptide, wherein said dinQ-derived polypeptide consists of a polypeptide selected from the group consisting of:
   (a) a polypeptide selected from the group consisting of, SEQ ID NO: 7, SEQ ID NO: 9, and SEQ ID NO: 11,
   (b) a functionally equivalent subsequence of (a) of at least 15 amino acids, and
   (c) a functionally equivalent polypeptide with a sequence identity of at least 85% to (a) or (b).

* * * * *

SEQUENCE LISTING

<160> NUMBER OF SEQ ID NOS: 33

<210> SEQ ID NO 1
<211> LENGTH: 378
<212> TYPE: DNA
<213> ORGANISM: Escherichia coli
<220> FEATURE:
<221> NAME/KEY: protein_bind
<222> LOCATION: (6)..(25)
<223> OTHER INFORMATION: lexA box 1
<220> FEATURE:
<221> NAME/KEY: -35_signal
<222> LOCATION: (9)..(14)
<220> FEATURE:
<221> NAME/KEY: protein_bind
<222> LOCATION: (28)..(47)
<223> OTHER INFORMATION: lexA box 2
<220> FEATURE:
<221> NAME/KEY: -10_signal
<222> LOCATION: (33)..(38)
<220> FEATURE:
<221> NAME/KEY: misc_binding
<222> LOCATION: (132)..(165)
<223> OTHER INFORMATION: agrAB repeat
<220> FEATURE:
<221> NAME/KEY: terminator
<222> LOCATION: (338)..(351)
<220> FEATURE:
<221> NAME/KEY: terminator
<222> LOCATION: (356)..(369)

<400> SEQUENCE: 1

```
ggacgtgctg gttttataac ctgcatgtac tgtatgatta ccagttagc tctgaggcat      60
tttcactctg gcaatgcgca taaacgcttt caaagtcctg gtcagaagta cgggtggtgc    120
cgttaactga tgctctggcc ggagtgagag agttcttatc taacaatgag acatgcgccg    180
tgacaggcag tggatgagta agcggatgca ttctcactcc atcgcatgga gaaaacgggt    240
gattgataaa gcaatcatcg ttctaggggc gttaattgcg ctgctggaac tgatccgctt    300
tctgcttcag cttctgaact gatagcggaa acgtaattaa gggctaagag cacactactc    360
ttagcccttt aacattta                                                  378
```

<210> SEQ ID NO 2
<211> LENGTH: 57
<212> TYPE: DNA
<213> ORGANISM: Escherichia coli
<220> FEATURE:
<221> NAME/KEY: CDS
<222> LOCATION: (1)..(57)

<400> SEQUENCE: 2

```
atg cgc ata aac gct ttc aaa gtc ctg gtc aga agt acg ggt ggt gcc       48
Met Arg Ile Asn Ala Phe Lys Val Leu Val Arg Ser Thr Gly Gly Ala
1               5                   10                  15 gtt aac tga                                                           57
Val Asn
```

<210> SEQ ID NO 3
<211> LENGTH: 18
<212> TYPE: PRT
<213> ORGANISM: Escherichia coli

<400> SEQUENCE: 3

```
Met Arg Ile Asn Ala Phe Lys Val Leu Val Arg Ser Thr Gly Gly Ala
1               5                   10                  15

Val Asn
```

```
<210> SEQ ID NO 4
<211> LENGTH: 150
<212> TYPE: DNA
<213> ORGANISM: Escherichia coli
<220> FEATURE:
<221> NAME/KEY: CDS
<222> LOCATION: (1)..(150)

<400> SEQUENCE: 4 atg cgc cgt gac agg cag tgg atg agt aag cgg atg cat tct cac tcc       48
Met Arg Arg Asp Arg Gln Trp Met Ser Lys Arg Met His Ser His Ser
1               5                   10                  15 atc gca tgg aga aaa cgg gtg att gat aaa gca atc atc gtt cta ggg       96
Ile Ala Trp Arg Lys Arg Val Ile Asp Lys Ala Ile Ile Val Leu Gly
                20                  25                  30 gcg tta att gcg ctg ctg gaa ctg atc cgc ttt ctg ctt cag ctt ctg      144
Ala Leu Ile Ala Leu Leu Glu Leu Ile Arg Phe Leu Leu Gln Leu Leu
            35                  40                  45 aac tga                                                               150
Asn

<210> SEQ ID NO 5
<211> LENGTH: 49
<212> TYPE: PRT
<213> ORGANISM: Escherichia coli

<400> SEQUENCE: 5

Met Arg Arg Asp Arg Gln Trp Met Ser Lys Arg Met His Ser His Ser
1               5                   10                  15

Ile Ala Trp Arg Lys Arg Val Ile Asp Lys Ala Ile Ile Val Leu Gly
                20                  25                  30

Ala Leu Ile Ala Leu Leu Glu Leu Ile Arg Phe Leu Leu Gln Leu Leu
            35                  40                  45

Asn

<210> SEQ ID NO 6
<211> LENGTH: 129
<212> TYPE: DNA
<213> ORGANISM: Escherichia coli
<220> FEATURE:
<221> NAME/KEY: CDS
<222> LOCATION: (1)..(129)

<400> SEQUENCE: 6 atg agt aag cgg atg cat tct cac tcc atc gca tgg aga aaa cgg gtg       48
Met Ser Lys Arg Met His Ser His Ser Ile Ala Trp Arg Lys Arg Val
1               5                   10                  15 att gat aaa gca atc atc gtt cta ggg gcg tta att gcg ctg ctg gaa       96
Ile Asp Lys Ala Ile Ile Val Leu Gly Ala Leu Ile Ala Leu Leu Glu
                20                  25                  30 ctg atc cgc ttt ctg ctt cag ctt ctg aac tga                          129
Leu Ile Arg Phe Leu Leu Gln Leu Leu Asn
            35                  40

<210> SEQ ID NO 7
<211> LENGTH: 42
<212> TYPE: PRT
<213> ORGANISM: Escherichia coli

<400> SEQUENCE: 7

Met Ser Lys Arg Met His Ser His Ser Ile Ala Trp Arg Lys Arg Val
1               5                   10                  15
```

Ile Asp Lys Ala Ile Ile Val Leu Gly Ala Leu Ile Ala Leu Leu Glu
            20                  25                  30

Leu Ile Arg Phe Leu Leu Gln Leu Leu Asn
        35                  40

<210> SEQ ID NO 8
<211> LENGTH: 117
<212> TYPE: DNA
<213> ORGANISM: Escherichia coli
<220> FEATURE:
<221> NAME/KEY: CDS
<222> LOCATION: (1)..(117)

<400> SEQUENCE: 8 atg cat tct cac tcc atc gca tgg aga aaa cgg gtg att gat aaa gca    48
Met His Ser His Ser Ile Ala Trp Arg Lys Arg Val Ile Asp Lys Ala
1               5                   10                  15 atc atc gtt cta ggg gcg tta att gcg ctg ctg gaa ctg atc cgc ttt    96
Ile Ile Val Leu Gly Ala Leu Ile Ala Leu Leu Glu Leu Ile Arg Phe
            20                  25                  30 ctg ctt cag ctt ctg aac tga                                       117
Leu Leu Gln Leu Leu Asn
        35

<210> SEQ ID NO 9
<211> LENGTH: 38
<212> TYPE: PRT
<213> ORGANISM: Escherichia coli

<400> SEQUENCE: 9

Met His Ser His Ser Ile Ala Trp Arg Lys Arg Val Ile Asp Lys Ala
1               5                   10                  15

Ile Ile Val Leu Gly Ala Leu Ile Ala Leu Leu Glu Leu Ile Arg Phe
            20                  25                  30

Leu Leu Gln Leu Leu Asn
        35

<210> SEQ ID NO 10
<211> LENGTH: 84
<212> TYPE: DNA
<213> ORGANISM: Escherichia coli
<220> FEATURE:
<221> NAME/KEY: CDS
<222> LOCATION: (1)..(84)

<400> SEQUENCE: 10 gtg att gat aaa gca atc atc gtt cta ggg gcg tta att gcg ctg ctg    48
Val Ile Asp Lys Ala Ile Ile Val Leu Gly Ala Leu Ile Ala Leu Leu
1               5                   10                  15 gaa ctg atc cgc ttt ctg ctt cag ctt ctg aac tga                    84
Glu Leu Ile Arg Phe Leu Leu Gln Leu Leu Asn
            20                  25

<210> SEQ ID NO 11
<211> LENGTH: 27
<212> TYPE: PRT
<213> ORGANISM: Escherichia coli

<400> SEQUENCE: 11

Val Ile Asp Lys Ala Ile Ile Val Leu Gly Ala Leu Ile Ala Leu Leu
1               5                   10                  15

Glu Leu Ile Arg Phe Leu Leu Gln Leu Leu Asn
            20                  25

<210> SEQ ID NO 12
<211> LENGTH: 85
<212> TYPE: DNA
<213> ORGANISM: Escherichia coli

<400> SEQUENCE: 12
gttagatgat ggctatctca ctccagtcag agccaccaac tcagggctgg aaagtaaaaa      60
accgacgcaa agtcggtttt tttac                                            85

<210> SEQ ID NO 13
<211> LENGTH: 86
<212> TYPE: DNA
<213> ORGANISM: Escherichia coli

<400> SEQUENCE: 13
tgttagataa gaactctctc actccagcca gagccaccaa ctcagggctg aaagtaaaa       60 aaccgacgca agtcggttt ttttac                                            86

<210> SEQ ID NO 14
<211> LENGTH: 330
<212> TYPE: DNA
<213> ORGANISM: Escherichia coli

<400> SEQUENCE: 14
ttagctctga ggcattttca ctctggcaat gcgcataaac gctttcaaag tcctggtcag      60
aagtacgggt ggtgccgtta actgatgctc tggccggagt gagagagttc ttatctaaca     120
atgagacatg cgccgtgaca ggcagtggat gagtaagcgg atgcattctc actccatcgc     180
atggagaaaa cgggtgattg ataaagcaat catcgttcta ggggcgttaa ttgcgctgct     240
ggaactgatc cgctttctgc ttcagcttct gaactgatag cggaaacgta attaagggct     300
aagagcacac tactcttagc cctttaacat                                      330

<210> SEQ ID NO 15
<211> LENGTH: 287
<212> TYPE: DNA
<213> ORGANISM: Escherichia coli

<400> SEQUENCE: 15
ttcaaagtcc tggtcagaag tacgggtggt gccgttaact gatgctctgg ccggagtgag     60
agagttctta tctaacaatg agacatgcgc cgtgacaggc agtggatgag taagcggatg    120
cattctcact ccatcgcatg gagaaaacgg gtgattgata aagcaatcat cgttctaggg    180
gcgttaattg cgctgctgga actgatccgc tttctgcttc agcttctgaa ctgatagcgg    240
aaacgtaatt aagggctaag agcacactac tcttagccct ttaacat                  287

<210> SEQ ID NO 16
<211> LENGTH: 209
<212> TYPE: DNA
<213> ORGANISM: Escherichia coli

<400> SEQUENCE: 16
tgagacatgc gccgtgacag gcagtggatg agtaagcgga tgcattctca ctccatcgca    60
tggagaaaac gggtgattga taaagcaatc atcgttctag gggcgttaat tgcgctgctg    120
gaactgatcc gctttctgct tcagcttctg aactgatagc ggaaacgtaa ttaagggcta    180
agagcacact actcttagcc ctttaacat                                      209

```
<210> SEQ ID NO 17
<211> LENGTH: 27
<212> TYPE: PRT
<213> ORGANISM: Escherichia coli

<400> SEQUENCE: 17

Met Ile Asp Lys Ala Ile Ile Val Leu Gly Ala Leu Ile Ala Leu Leu
1               5                   10                  15

Glu Leu Ile Arg Phe Leu Leu Gln Leu Leu Asn
            20                  25

<210> SEQ ID NO 18
<211> LENGTH: 3094
<212> TYPE: DNA
<213> ORGANISM: Artificial Sequence
<220> FEATURE:
<223> OTHER INFORMATION: plasmid pORF5

<400> SEQUENCE: 18
agcttccaca cattatattg ttatccgctc acaatgtcaa ttggaaattt aaaataattt      60
tctgaggatc cactagttct agagcggccg ccaccgcggt ggctgcatta atgaatcggc     120
caacgcgcgg ggagaggcgg tttgcgtatt gggcgctctt ccgcttcctc gctcactgac     180
tcgctgcgct cggtcgttcg gctgcggcga gcggtatcag ctcactcaaa ggcggtaata     240
cggttatcca cagaatcagg ggataacgca ggaaagaaca tgtgagcaaa aggccagcaa     300
aaggccagga accgtaaaaa ggccgcgttg ctggcgtttt tccataggct ccgcccccct     360
gacgagcatc acaaaaatcg acgctcaagt cagaggtggc gaaacccgac aggactataa     420
agataccagg cgtttccccc tggaagctcc ctcgtgcgct ctcctgttcc gaccctgccg     480
cttaccggat acctgtccgc ctttctccct tcgggaagcg tggcgctttc tcatagctca     540
cgctgtaggt atctcagttc ggtgtaggtc gttcgctcca agctgggctg tgtgcacgaa     600
ccccccgttc agcccgaccg ctgcgcctta tccggtaact atcgtcttga gtccaacccg     660
gtaagacacg acttatcgcc actggcagca gccactggta acaggattag cagagcgagg     720
tatgtaggcg gtgctacaga gttcttgaag tggtggccta actacggcta cactagaagg     780
acagtatttg gtatctgcgc tctgctgaag ccagttacct tcggaaaaag agttggtagc     840
tcttgatccg gcaaacaaac caccgctggt agcggtggtt tttttgtttg caagcagcag     900
attacgcgca gaaaaaaagg atctcaagaa gatcctttga tcttttctac ggggtctgac     960
gctcagtgga acgaaaactc acgttaaggg attttggtca tgagattatc aaaaaggatc    1020
ttcacctaga tccttttaaa ttaaaaatga agttttaaat caatctaaag tatatatgag    1080
taaacttggt ctgacagtta ccaatgctta atcagtgagg cacctatctc agcgatctgt    1140
ctatttcgtt catccatagt tgcctgactc cccgtcgtgt agataactac gatacgggag    1200
ggcttaccat ctggccccag tgctgcaatg ataccgcgag acccacgctc accggctcca    1260
gatttatcag caataaacca gccagccgga agggccgagc gcagaagtgg tcctgcaact    1320
ttatccgcct ccatccagtc tattaattgt tgccgggaag ctagagtaag tagttcgcca    1380
gttaatagtt tgcgcaacgt tgttgccatt gctacaggca tcgtggtgtc acgctcgtcg    1440
tttggtatgg cttcattcag ctccggttcc caacgatcaa ggcgagttac atgatccccc    1500
atgttgtgca aaaaagcggt tagctccttc ggtcctccga tcgttgtcag aagtaagttg    1560
gccgcagtgt tatcactcat ggttatggca gcactgcata attctcttac tgtcatgcca    1620
tccgtaagat gcttttctgt gactggtgag tactcaacca agtcattctg agaatagtgt    1680
```

-continued

```
atgcggcgac cgagttgctc ttgcccggcg tcaatacggg ataataccgc gccacatagc    1740
agaactttaa aagtgctcat cattggaaaa cgttcttcgg ggcgaaaact ctcaaggatc    1800
ttaccgctgt tgagatccag ttcgatgtaa cccactcgtg cacccaactg atcttcagca    1860
tcttttactt tcaccagcgt ttctgggtga gcaaaaacag gaaggcaaaa tgccgcaaaa    1920
aagggaataa gggcgacacg gaaatgttga atactcatac tcttcctttt tcaatattat    1980
tgaagcattt atcagggtta ttgtctcatg agcggataca tatttgaatg tatttagaaa    2040
aataaacaaa taggggttcc gcgcacattt ccccgaaaag tgccacctaa attgtaagcg    2100
ttaatatttt gttaaaattc gcgttaaatt tttgttaaat cagctcattt tttaaccaat    2160
aggccgaaat cggcaaaatc ccttataaat caaaagaata gaccgagata gggttgagtg    2220
ttgttccagt ttggaacaag agtccactat taaagaacgt ggactccaac gtcaaagggc    2280
gaaaaaccgt ctatcagggc gatggcccac tacgtgaacc atcaccctaa tcaagttttt    2340 tgggtcgag gtgccgtaaa gcactaaatc ggaaccctaa agggagcccc cgatttagag    2400
cttgacgggg aaagccggcg aacgtggcga gaaaggaagg gaagaaagcg aaaggagcgg    2460
gcgctagggc gctggcaagt gtagcggtca cgctgcgcgt aaccaccaca cccgccgcgc    2520
ttaatgcgcc gctacagggc gcgtcccatt cgccattcag gctgcgcaac tgttgggaag    2580
ggcgatcggt gcgggcctct tcgctattac gccagctggc gaaaggggga tgtgctgcaa    2640
ggcgattaag ttgggtaacg ccagggtttt cccagtcacg acgttgtaaa acgacggcca    2700
gtgagcgcgc gtaatacgac tcactatagg gcgaattggg taccgggccc ccctcgacg    2760 cgtaaaaaaa cccgccgggg cgggtttttt tacgcgtcga ggaagtgccg gatccgaaaa    2820
gaagaactaa ctcgttgtgg agaataacaa aaatggtcat ctggagctta caggtggcca    2880
ttcgtgggac agtatccctg acagcctaca aaacgcaatt gaagaacgcg aggcatcgtc    2940
ttaacgaggc accgaggcgt cgcattcttc agatggttca acccttaagc ggatcctcag    3000
ttcagaagct gaagcagaaa gcggatcagt tccagcagcg caattaacgc ccctagaacg    3060
atgattgctt tatcaaccat ccgttttcct ccta                                3094
```

<210> SEQ ID NO 19
<211> LENGTH: 27
<212> TYPE: PRT
<213> ORGANISM: Artificial Sequence
<220> FEATURE:
<223> OTHER INFORMATION: G10K variant of dinQ ORF V peptide

<400> SEQUENCE: 19

Met Ile Asp Lys Ala Ile Ile Val Leu Lys Ala Leu Ile Ala Leu Leu
1               5                   10                  15

Glu Leu Ile Arg Phe Leu Leu Gln Leu Leu Asn
            20                  25

<210> SEQ ID NO 20
<211> LENGTH: 27
<212> TYPE: PRT
<213> ORGANISM: Artificial Sequence
<220> FEATURE:
<223> OTHER INFORMATION: L23I variant of dinQ ORF V peptide

<400> SEQUENCE: 20

Met Ile Asp Lys Ala Ile Ile Val Leu Gly Ala Leu Ile Ala Leu Leu
1               5                   10                  15

Glu Leu Ile Arg Phe Leu Ile Gln Leu Leu Asn
            20                  25

```
<210> SEQ ID NO 21
<211> LENGTH: 27
<212> TYPE: PRT
<213> ORGANISM: Artificial Sequence
<220> FEATURE:
<223> OTHER INFORMATION: I7V variant of dinQ ORF V peptide

<400> SEQUENCE: 21

Met Ile Asp Lys Ala Ile Val Val Leu Gly Ala Leu Ile Ala Leu Leu
1               5                   10                  15

Glu Leu Ile Arg Phe Leu Leu Gln Leu Leu Asn
            20                  25

<210> SEQ ID NO 22
<211> LENGTH: 27
<212> TYPE: PRT
<213> ORGANISM: Artificial Sequence
<220> FEATURE:
<223> OTHER INFORMATION: double mutant variant (L12I,I13V) of dinQ ORF V
      peptide

<400> SEQUENCE: 22

Met Ile Asp Lys Ala Ile Ile Val Leu Gly Ala Ile Val Ala Leu Leu
1               5                   10                  15

Glu Leu Ile Arg Phe Leu Leu Gln Leu Leu Asn
            20                  25

<210> SEQ ID NO 23
<211> LENGTH: 753
<212> TYPE: DNA
<213> ORGANISM: Escherichia coli

<400> SEQUENCE: 23
taaatgttaa agggctaaga gtagtgtgct cttagccctt aattacgttt ccgctatcag      60
ttcagaagct gaagcagaaa gcggatcagt tccagcagcg caattaacgc ccctagaacg     120
atgattgctt tatcaatcac ccgttttctc catgcgatgg agtgagaatg catccgctta     180
ctcatccact gcctgtcacg gcgcatgtct cattgttaga taagaactct ctcactccgg     240
ccagagcatc agttaacggc accacccgta cttctgacca ggactttgaa agcgtttatg     300
cgcattgcca gagtgaaaat gcctcagagc taactggata atcatacagt acatgcaggt     360
tataaaacca gcacgtcctt gcaatagttt cagtatggta ttagcattga tgcgttagat     420
gatggctatc tcactccagt cagagccacc aactcagggc tggaaagtaa aaaaccgacg     480
caaagtcggt ttttttacat ccggattcgg acaaggctta atatgacgat gacccagtga     540
aagtatataa atcgtcactg cgatatatac cgaagtgctc cctccgccag ctgaagaaat     600
cgctaattct tgcaatgtta gccactggct aatagtattg agctgttaga taagaactct     660
ctcactccag ccagagccac caactcaggg ctggaaagta aaaaaccgac gcaaagtcgg     720
ttttttacg tcctgattca gacctccttt caa                                  753

<210> SEQ ID NO 24
<211> LENGTH: 331
<212> TYPE: DNA
<213> ORGANISM: Escherichia coli

<400> SEQUENCE: 24
gttagctctg aggcattttc actctggcaa tgcgcataaa cgctttcaaa gtcctggtca      60
gaagtacggg tggtgccgtt aactgatgct ctggccggag tgagagagtt cttatctaac     120
```

```
aatgagacat gcgccgtgac aggcagtgga tgagtaagcg gatgcattct cactccatcg      180
catggagaaa acgggtgatt gataaagcaa tcatcgttct aggggcgtta attgcgctgc      240
tggaactgat ccgctttctg cttcagcttc tgaactgata gcggaaacgt aattaagggc      300
taagagcaca ctactcttag ccctttaaca t                                    331
```

<210> SEQ ID NO 25
<211> LENGTH: 105
<212> TYPE: DNA
<213> ORGANISM: Escherichia coli

<400> SEQUENCE: 25

```
tgatgcgtta gatgatggct atctcactcc agtcagagcc accaactcag ggctggaaag       60
taaaaaaccg acgcaaagtc ggttttttta catccggatt cggac                      105
```

<210> SEQ ID NO 26
<211> LENGTH: 105
<212> TYPE: DNA
<213> ORGANISM: Escherichia coli

<400> SEQUENCE: 26

```
tgagctgtta gataagaact ctctcactcc agccagagcc accaactcag ggctggaaag       60
taaaaaaccg acgcaaagtc ggttttttta cgtcctgatt cagac                      105
```

<210> SEQ ID NO 27
<211> LENGTH: 34
<212> TYPE: DNA
<213> ORGANISM: Escherichia coli

<400> SEQUENCE: 27

```
tgttagataa gaactctctc actccggcca gagc                                   34
```

<210> SEQ ID NO 28
<211> LENGTH: 47
<212> TYPE: DNA
<213> ORGANISM: Artificial Sequence
<220> FEATURE:
<223> OTHER INFORMATION: From gel in Fig 2B

<400> SEQUENCE: 28

```
gagactccgt aaaagtgaga ccgttacaca tatttgcgaa agtttca                     47
```

<210> SEQ ID NO 29
<211> LENGTH: 21
<212> TYPE: DNA
<213> ORGANISM: Artificial Sequence
<220> FEATURE:
<223> OTHER INFORMATION: Sequence on gel (Fig 2C left)

<400> SEQUENCE: 29

```
gtaactacac aatctactac c                                                 21
```

<210> SEQ ID NO 30
<211> LENGTH: 22
<212> TYPE: DNA
<213> ORGANISM: Artificial Sequence
<220> FEATURE:
<223> OTHER INFORMATION: Sequence on gel (Fig 2C right)

```
<400> SEQUENCE: 30
tatcataact cgacaatcta tt                                                    22

<210> SEQ ID NO 31
<211> LENGTH: 81
<212> TYPE: RNA
<213> ORGANISM: Escherichia coli

<400> SEQUENCE: 31
guacgcaaug uguuaugcgg gggccgcauc guuacccggc gcacuaaguc cuggcugaaa            60
cggguggugc cgucagcgcc u                                                     81

<210> SEQ ID NO 32
<211> LENGTH: 89
<212> TYPE: RNA
<213> ORGANISM: Escherichia coli

<400> SEQUENCE: 32
caguuagcuc ugaggcauuu ucacucuggc aaugcgcaua aacgcuuuca aaguccuggu            60
cagaaguacg gguggugccg uuaacugau                                             89

<210> SEQ ID NO 33
<211> LENGTH: 27
<212> TYPE: PRT
<213> ORGANISM: Escherichia coli

<400> SEQUENCE: 33

Met Ile Asp Lys Ala Ile Ile Val Lys Gly Ala Leu Ile Ala Leu Leu
1               5                   10                  15

Glu Leu Ile Arg Phe Leu Leu Gln Leu Leu Asn
            20                  25
```